US008864713B2

(12) United States Patent
D'Antonio et al.

(10) Patent No.: US 8,864,713 B2
(45) Date of Patent: Oct. 21, 2014

(54) HYPODERMIC INJECTION SYSTEM

(75) Inventors: Nicholas F. D'Antonio, Tully, NY (US);
Nicholas J. D'Antonio, Tully, NY (US);
Richard O. Colvin, Baldwinsville, NY (US)

(73) Assignees: Genesis Instruments, Division of Genesis Industries, Inc., Elmwood, WI (US); Mark Anderson and Associates, Inc., Spring Valley, WI (US)

( * ) Notice: Subject to any disclaimer, the term of this patent is extended or adjusted under 35 U.S.C. 154(b) by 611 days.

(21) Appl. No.: 13/088,929

(22) Filed: Apr. 18, 2011

(65) Prior Publication Data

US 2011/0224613 A1    Sep. 15, 2011

Related U.S. Application Data

(63) Continuation of application No. 11/629,145, filed as application No. PCT/US2005/020268 on Jun. 9, 2005, now Pat. No. 7,927,307.

(60) Provisional application No. 60/578,455, filed on Jun. 9, 2004.

(51) Int. Cl.
*A61M 5/00* (2006.01)
*A61M 5/20* (2006.01)
*A61M 5/30* (2006.01)
A61M 5/315 (2006.01)
A61M 5/32 (2006.01)

(52) U.S. Cl.
CPC ..... *A61M 5/204* (2013.01); *A61M 2005/31588* (2013.01); *A61M 5/31546* (2013.01); *A61M 5/008* (2013.01); *A61M 5/31525* (2013.01); *A61M 2205/50* (2013.01); *A61M 5/3205* (2013.01); *A61M 5/30* (2013.01)
USPC ........................................ 604/152

(58) Field of Classification Search
USPC .................. 604/152–154, 114–115, 117–118
See application file for complete search history.

(56) References Cited

U.S. PATENT DOCUMENTS

| | | | |
|---|---|---|---|
| 5,049,143 A | 9/1991 | Gertner et al. | |
| 5,080,648 A | 1/1992 | D'Antonio | |
| 5,241,925 A | 9/1993 | Gertner et al. | |
| 5,318,522 A | 6/1994 | D'Antonio | |
| 5,569,190 A | 10/1996 | D'Antonio | |
| 5,616,132 A | 4/1997 | Newman | |
| 5,928,201 A | 7/1999 | Poulsen et al. | |
| 5,957,895 A | 9/1999 | Sage et al. | |
| 6,056,716 A | 5/2000 | D'Antonio et al. | |
| 6,997,906 B2 | 2/2006 | Langley et al. | |
| 2003/0040715 A1 | 2/2003 | D'Antonio et al. | |

FOREIGN PATENT DOCUMENTS

WO    WO 93/03779         3/1993
WO    WO 03/103751 A1    12/2003

*Primary Examiner* — Nicholas Lucchesi
*Assistant Examiner* — Melissa A Snyder
(74) *Attorney, Agent, or Firm* — Skinner and Associates; Joel Skinner

(57) ABSTRACT

The invention relates to a hypodermic injection system having a direct-drive motor for moving a ram towards an injectate chamber for discharging injectate therein through a discharge orifice. The system can have an injection head attached to a housing having an injectate chamber for holding injectate to be injected, a remote discharge device with a control apparatus or the structure for holding a cartridge containing injectate. The injectate supply could be a bottle, a remote reservoir or a cartridge. An injection head can have a nose actuator for enabling an injection only if the nose actuator has engaged the body to be injected. A clamping device clamps the body to be injected. Control is effected through a microprocessor to which the electrically-operated parts of the invention are attached. Control and output signals are readable through an electronic display.

27 Claims, 14 Drawing Sheets

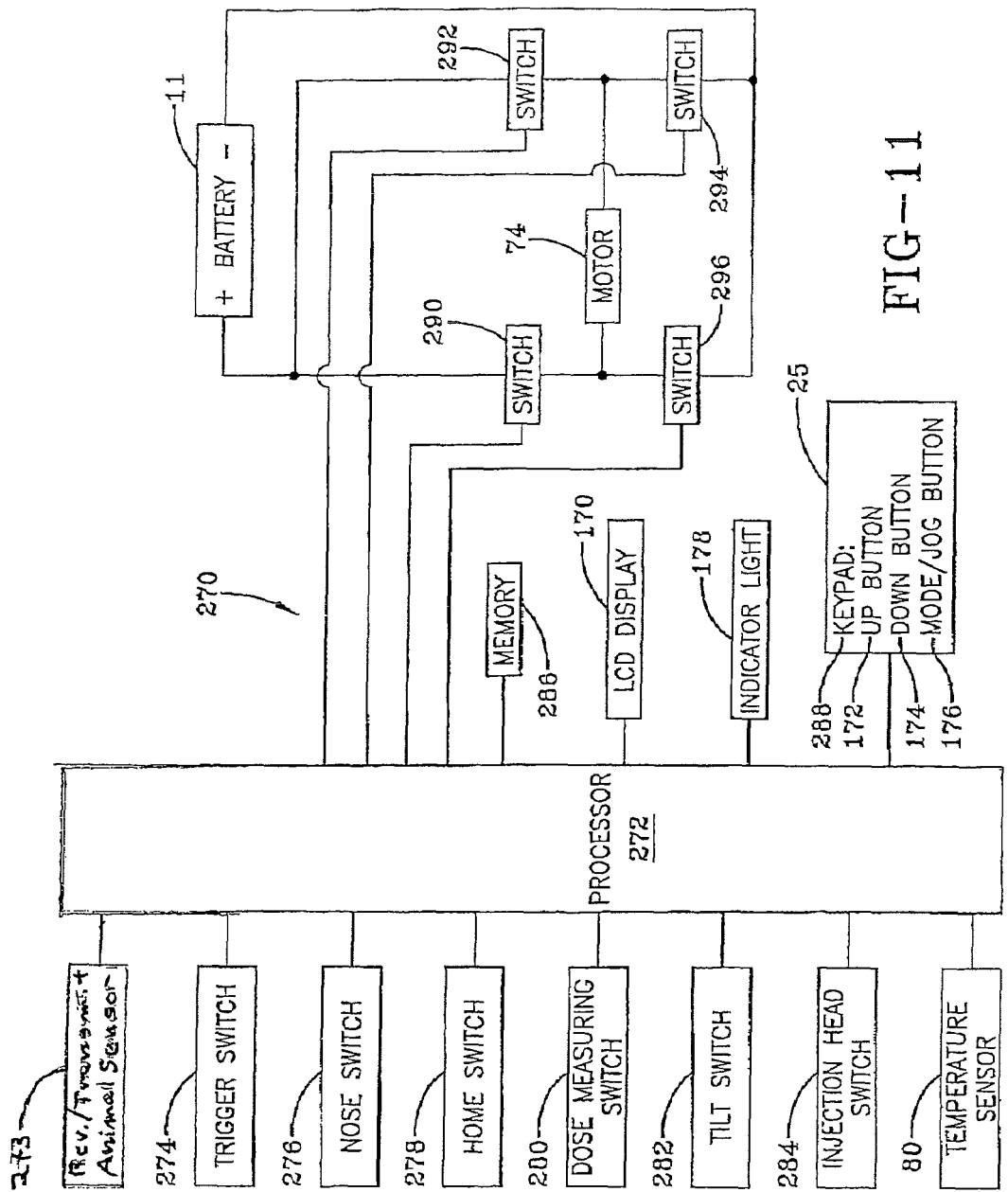

HYPODERMIC INJECTION SYSTEM

CROSS-REFERENCE TO RELATED APPLICATION

This application is a continuation of U.S. patent application Ser. No. 11/629,145, filed Dec. 8, 2006 (to be granted, U.S. Pat. No. 7,927,307, issue date Apr. 19, 2011), which is a U.S. National Phase Application of PCT/US2005/020268 filed Jun. 9, 2005, which claims priority of U.S. provisional patent application Ser. No. 60/578,455 filed Jun. 9, 2004.

BACKGROUND OF THE INVENTION

1. Field of the Invention

This invention relates to injectors, and in particular to a high-speed hypodermic injection system for injecting animals or people at predetermined depths of injection with various safety features.

2. Description of the Prior Art

Hypodermic injection systems have been developed for increasing the efficiency and effectiveness of injecting bodies of both animals and persons. Routine procedures against diseases and the possibility of pandemic or bioterror events makes the ability to have a high rate of injections very important in view of the vast numbers of injections to be made on herds of domestic animals such as cattle, goats, sheep, swine, chickens, turkeys and the like; water animals such as fish and shellfish including lobsters, shrimp, crabs and the like; and groups of persons such as school children, civilian populations, military forces, and the like. Furthermore, there are many problems to be contended with. Many bodies present difficulty in making effective injections due to the hair or fur, hair follicles, skin thickness, age of the species, their environment, etc. U.S. Pat. No. 6,056,716, incorporated herein by reference, successfully contends with many of these problems. It has been found that injections made to skin-covered bodies can be particularly effective and not damaging to the muscle beneath the skin if the injection begins as a well controlled jet stream in the dermal or subcutaneous regions, so that no needles ever penetrate the muscle during the delivery, and the foregoing U.S. Pat. No. 6,056,716 provides a perforator system for effecting the capability and effectiveness of such injections. A perforator system as used herein means an assembly having an injection shaft long enough to pierce the dermis or other outer covering of an animal or human, but not long enough to damage or otherwise affect the internal muscle of animals or humans, or otherwise extending much beyond the outer covering. Perforator systems have perforator shafts generally shorter than standard needles. While the importance and effectiveness of perforator delivery is clearly described in these prior art systems, they did not disclose the use of hubs from which the perforator shaft extends, which is different from hubs for standard needles, to totally prevent the use of standard needles whose length can reach 1.5 inches. The prior art did not deal with the issue of long needles that often bend, and even break, an event that sometime leaves a needle in the consumable portion of the animal, not to mention the pain to the animal or the scarring/abscesses they cause deep in the muscle, or the economic loss they incur to the producers. Furthermore, whereas hypodermic injection systems, especially for humans, have been a single dosage from a conventional needle and syringe, more effective systems using both cartridges holding injectate or injectate reservoirs were discussed in U.S. Pat. No. 6,056,716 and U.S. Pat. No. 5,569,190, also incorporated herein by reference. Greater control over the injection process is achieved using appropriate electromechanical devices, and the foregoing U.S. Pat. No. 6,056,716 discloses a direct-drive system that uses the motor force to implement an injection without first requiring the compression of a spring mechanism for applying the desired injection pressure.

Another problem particularly prevalent in animals is the likelihood of sudden movement just prior to or during an injection. No device has heretofore been available for disabling an injection if sudden movement occurs in the animal being injected, an event that could lead to a faulty injection that is both ineffective and damaging to the animal. Also, no device has heretofore been available where the perforator assembly is attached to a flexible coupling to further reduce the bending torque on the perforator hub assembly when working with aggressive animals.

Another aspect of hypodermic injection system technology is the failure heretofore of quickly and effectively changing delivery volumes over a range of values depending on the type of body being injected, the location of the injection and the nature of the injectate being delivered. Furthermore, prior electromechanical hypodermic injection systems did not provide such safety features as effective disablement if a battery supplying electric energy became depleted below a value capable of the desired injection parameters. Effective and efficient control of the potential damage from overheating has not been available on electro-mechanical hypodermic injection systems. Earlier hypodermic injection systems did not provide for a response to available information regarding the body temperature of the animal or person.

There are other shortcomings of earlier hypodermic injection systems which have not heretofore been effectively overcome, such as an identification system for advising what type of an injection or therapeutic procedure a particular animal or person needs and/or the necessary dosage required. There has been lacking a programmed control and identification system that restricts a particular injection system to one and only one compound such as immunosterilization products that must avoid contact with any other product.

Prior hypodermic injection systems have not been quite so diverse in field locations as that disclosed in the foregoing two patents, but a hypodermic injection system with such mobility and even wider capabilities as in the present invention have not been known at all. Furthermore, the prior art did not provide a variety of capabilities with an easy-to-use, highly-effective control system.

Various safety features for preventing needle sticks and for the safe disposal of needles or perforators have been made in the art. See for Example the foregoing U.S. Pat. Nos. 5,569,190 and 6,056,716. As further disclosed herein, improved protection at the time of use, as well as faster, safe disposal of needles or perforators is always desirable in hypodermic injection systems for injecting large numbers of bodies or making multiple injections in any number of bodies.

Prior art multi-shot hypodermic injection systems transfer or "pull" injectate from a vial for transfer to an injection chamber at the end of each injection cycle. The bottle or vial has a septum covering the opening to the bottle, and the prior art uses a septum spike for piercing the septum at the inside of a hub or rim surrounding the opening to allow access to the injectate fluid. The prior art has connections for securing the bottle in a fixed position to retain a secure seal with the septum, while at the same time assuring that the bottle cannot be pulled away during use. Securing the bottle is usually done in one of the following two ways. In one case, a vial retainer surrounds the bottle from top to bottom and attaches the bottle to the base of the septum spike. A screw or other means is used to apply force against the bottom of the bottle to press the hub of the bottle against the base of the spike. This arrangement is limited to the respective bottle sizes and requires a different vial retainer for each bottle size. A second method relies on the standard diameter and height of the bottle or vial hubs available. A gripping device is located directly behind the rear shoulder of the hub once the bottle is attached to the injection system to firmly secure the bottle in place during use. An advantage of the latter arrangement is that the hub size is standard. The prior art for the hub attachment arrangement relies on a resilient interference of a plastic or metal component which snaps into position behind the hub when it reaches the sloping point in the septum spike. The engagement or release of the bottle is achieved by a pulling or pushing force alone. Some designs require the user to apply a squeezing force on the retainer so as to open a pathway for the hub to pull off freely.

SUMMARY OF THE INVENTION

An object of the present invention is to provide a well-controlled hypodermic injection system which is capable of a large number of injections to the desired depth, at a high rate with predetermined dosages.

A further object is to provide a fast operating hypodermic injection system including new, improved set-up and maintenance times.

Another object of the present invention is to provide a hypodermic injection system capable of numerous ranges of injectate volumes that are easily variable within the selected ranges.

A still further object is to provide an injection system capable of making injections from a variety of fixed volumes for certain applications.

A further object is to provide a hypodermic injection system which provides information regarding important aspects of the injection process, such as the volume range presently available, and other selectable injection volumes within the active range, the active range being the minimum to maximum volumes of injectate then available to the injection system.

A still further object of the invention is the provision of a hypodermic injection system including an electromechanical injector system having a damage preventing disabling feature if overheating occurs.

A further object is the provision of a hypodermic injection system which is fully self-contained, but still provides for several thousand injection cycles with no need for an external power source.

An object is to provide a battery-operated electronic hypodermic injection system with a replaceable, rapidly rechargeable battery, therein reducing the number of batteries needed regardless of the most rapid, non-stop procedures possible.

Another object is to facilitate a change in injection delivery speed and/or penetrating ability by using battery packs at different voltages, or by electronically controlling the voltage output characteristics of a standard voltage pack.

A related object of the hypodermic injection system is the provision of a battery-operated injector system having a warning device if the battery charge falls too far below the intended value for providing the desired injection results.

An additional object of the present invention is the provision of an improved hypodermic injection system housing for mounting an injectate bottle or vial which is fast and simple to operate. and leak-free in operation.

Another object of the invention is to provide a hypodermic injection system having an orientation control for disabling the injector refill cycle unless it is in a proper orientation, for the purpose of preventing air from entering the injection chamber while operating in the bottle-feed mode.

It is another object to provide a hypodermic injection system having an easy-to-use control apparatus, for example, one that can be programmed to receive, identify, and be enabled to operate with one and only one type of compound.

Another object is to provide a lightweight, portable and ergonomically-designed hypodermic injection system.

It is an additional object to provide a hypodermic injection system requiring little physical effort on behalf of the operator.

A still further object is the provision of an improved hypodermic jet injection system.

It is a further object to provide a hypodermic injection system with a resettable counter for indicating the number of doses given of a particular injectate, or by a particular worker, a particular crew, or the number of injection at a particular location.

A related object is the provision of a hypodermic injection system for indicating the cumulative number of injections given since the device was first assembled.

It is another object of the invention to provide a hypodermic injection system having interchangeable heads providing the for different ranges of injectate volume, while also providing for supplying different amounts of injectate within the selected range, or alternatively, providing the option for interchangeable heads at different fixed volumes.

A yet additional object of the invention is to provide a hypodermic injection system for supplying each injection injectate from interchangeable reservoirs, the system having various unique capabilities.

Another object is to provide a hypodermic injection system having a remote handpiece, with a remote activating apparatus for delivery at space constrained or otherwise difficult locations.

A further object of the hypodermic injection system is to provide a device for clamping a holding apparatus on the skin of a body and effecting an injection at a prescribed depth either in the dermis or below the dermis.

A further related object of the hypodermic injection system is to provide a device that can only be energized for an injection if certain predetermined conditions for injection site contact are met.

It is another object to provide a hypodermic injection system for reducing pain to the animal or person being injected.

An additional object is to provide a hypodermic injection system for animals which does not damage the meat of the animal while producing rapid, effective and efficient injections utilizing apparatus for preventing the likelihood of leak back from the injection site.

An additional object of the hypodermic injection system is to provide an injector having an easy-to-read display and easy-to-control apparatus for reading and controlling a variety of factors relating to injections being given and the body being injected.

A still other object of the invention is to provide a hypodermic injection system having a housing with an, access port for receiving a disposable perforator-holding and discarding apparatus which is used to safely install a new perforator that is firmly held on the housing during use, and thereafter, for easily, safely and properly removing the used perforators from the housing for safe storage.

It is a further objective of the invention to provide a hypodermic injection system that will only receive perforators with perforator hubs which are different from needle hubs to fully avoid both the use of standard-length needles, the deep muscle damage standard-length needles cause, and the pain standard-length needles provoke in an animal.

It is also an object of the present invention to provide a hypodermic injection system with a removable and interchangeable head for changing the dosage range of injections, having an easily installed clamp structure to clamp the skin or other appendage or part of the body of an animal or person for easily and effectively making intradermal and subcutaneous injections with improved safety to the person making the injection.

A related object is to provide a clamping structure for interchangeable heads for different fixed dosages for use with a hypodermic injection system.

Another object of the invention is to provide a hypodermic injection system for obtaining information from tagged or otherwise labeled information on an animal or person for providing controlling signals to the system as to what type of injectate and the amount of injectate to be administered to the animal or person.

A further object is to provide a hypodermic injection system for acquiring information about the body of an animal or person such as its temperature and when it is most effective to make a particular injection.

Still another object is to provide a hypodermic injection system which can be interrupted during an injection cycle, such as when the body being injected either inadvertently, or intentionally moves far enough away to disengage the injection site nose actuator, but is then continued when the person giving the injection fully reengages the body and the nose actuator.

An additional object of the invention is the provision of a highly variable, yet a lightweight and compact hypodermic injection system.

A related object is the provision of a variable, electrically-driven injection system having a weight of less than 1.5 pounds with no battery installed, two pounds with a several thousand cycle battery connected, approximately six inches in length with no injection head, and ten inches in length with a 5 cc injection head installed.

A general object of the invention is the provision of an effective, efficient, variable hypodermic injection system.

The invention has been described in its preferred forms, but variations and modifications within the spirit and scope of the invention may occur to those skilled in the art from the following description and in the appended claims.

BRIEF DESCRIPTION OF THE DRAWINGS

FIG. 11 is a circuit drawing in block form of the electronic components of the hypodermic injection system shown in FIG. 1.

DETAILED DESCRIPTION OF THE INVENTION

Figure 1:
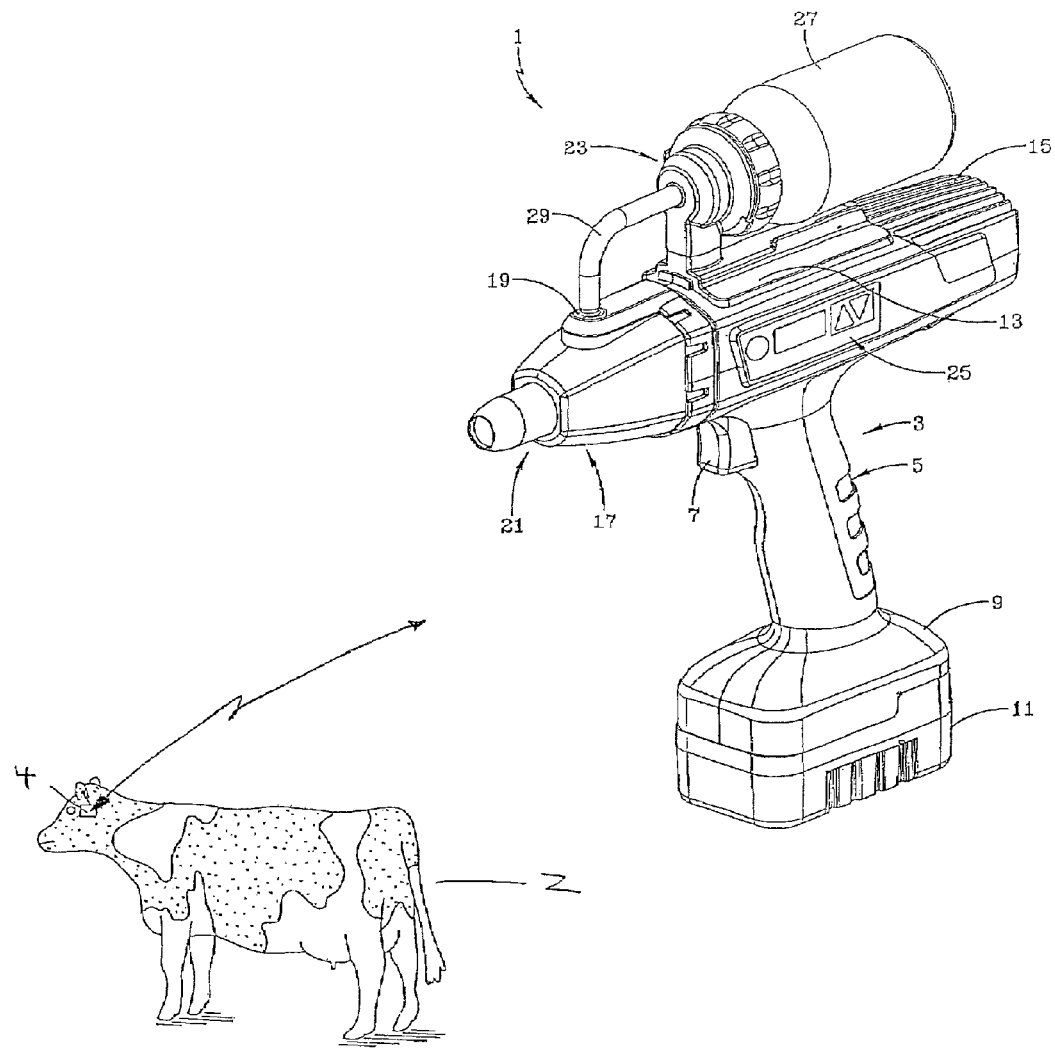
FIG. 1 is a perspective view of a hypodermic injection system according to one embodiment of the invention holding a vial or bottle containing an injectate.

Turning first to FIG. 1, a hypodermic injection system 1 according to an embodiment of the invention is shown. System 1 includes a housing 3 for housing various items including a drive assembly discussed below. Housing 3 has a handle 5 with a finger trigger 7, a base 9 to which a battery 11 is attached, an upper portion 13 for holding a motor as described below and a motor heat sink 15, an injection head coupling assembly discussed below to which an injection head 17 is attached having an injectate input port 19 and a nose trigger or nose shield 21 (containing a contact trigger actuator discussed below), a bottle carriage assembly 23 and an input control selector and control display 25. A bottle or vial 27 for supplying injectate is shown attached to carriage assembly 23, and an output tube 29 runs from bottle 27 to injection input port 19.

Figure 2:
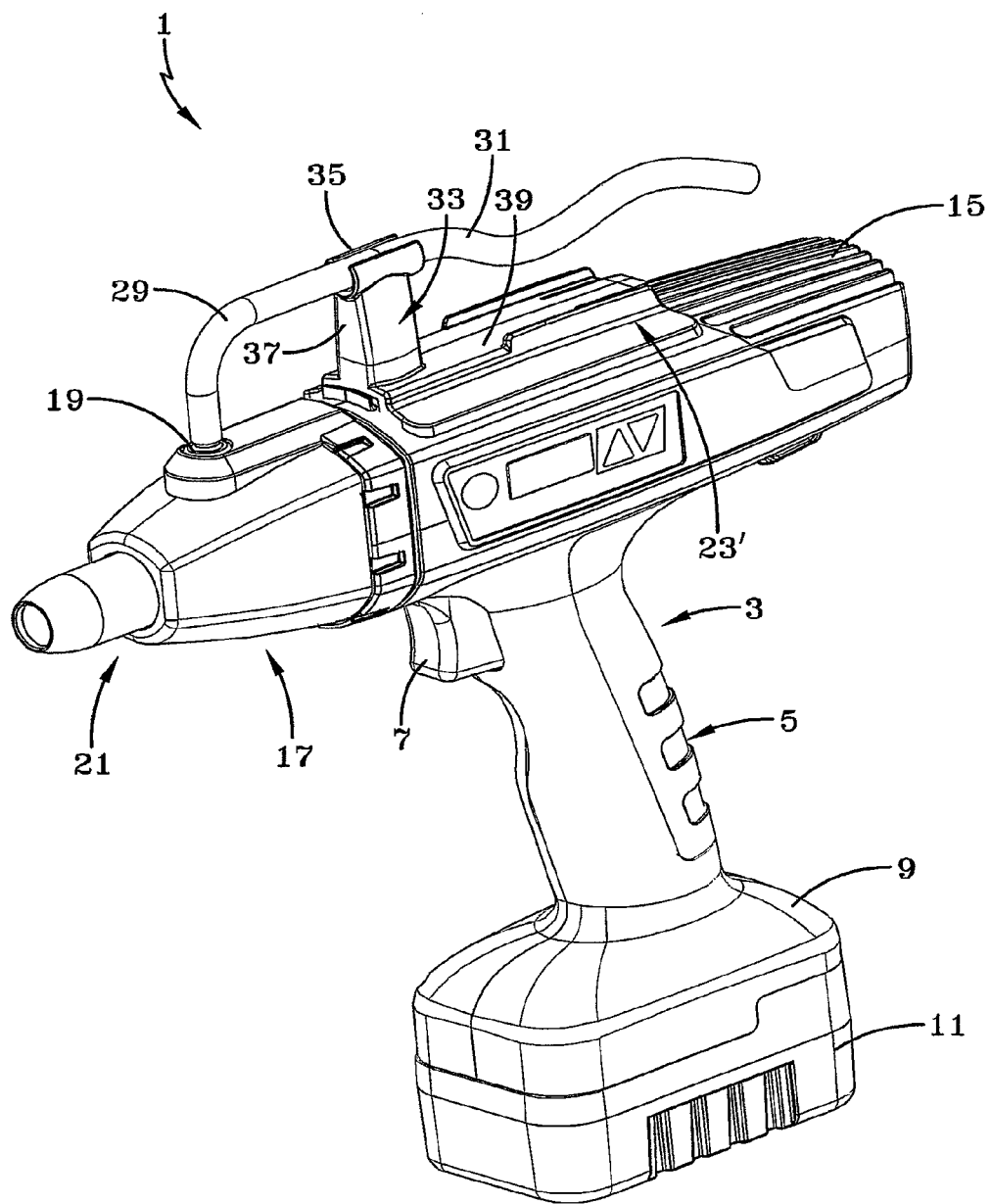
FIG. 2 is a perspective view of the hypodermic injection system shown in FIG. 1 having a line feed from a remote supply of an injectate.

FIG. 2 shows hypodermic injection system 1, but in this case bottle 27 is replaced by a remote supply (not shown) from which a remote injectate feed line 31 runs and is attached to input port 19. A tube holder 33 with a slotted cylindrical guide 35 extending from an upstanding arm 37 protrudes from a carriage base 39 of carriage assembly 23'. Carriage assembly 23' with tube holder 33 is removable, and is replaceable with carriage assembly 23. The remote supply could be located almost anywhere and could be a container disposed on the wall where injection procedures are done, at a building or other nearby facility, a tank which could be carried by a vehicle, in the user's waist belt, an arm holster or backpack, a portable tank, or an injectate-holding hollow belt.

Figure 3:
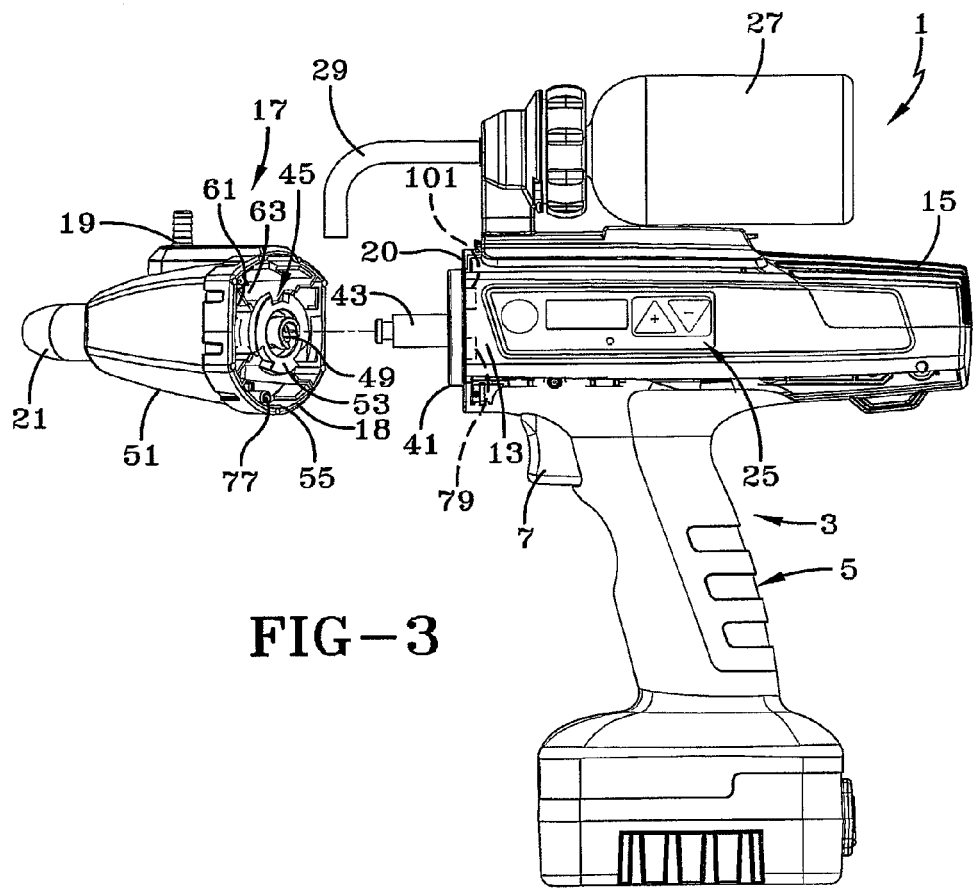
FIG. 3 is a perspective view of the hypodermic injection system shown in FIG. 1 showing an injection head decoupled from a housing holding the drive assembly of the system.
Figure 3A:
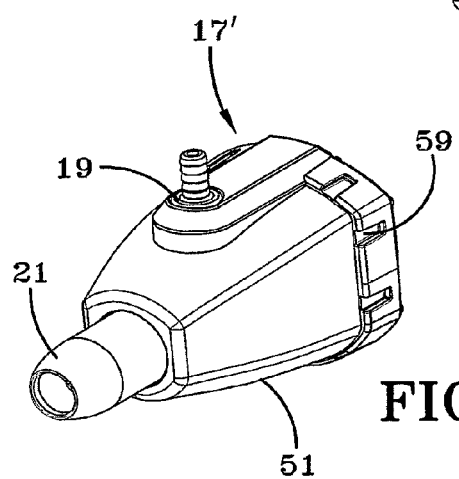
FIG. 3a is a perspective view of a hypodermic injection system head for holding a different capacity of injectate than the injection head shown in FIG. 3.
Figure 4:
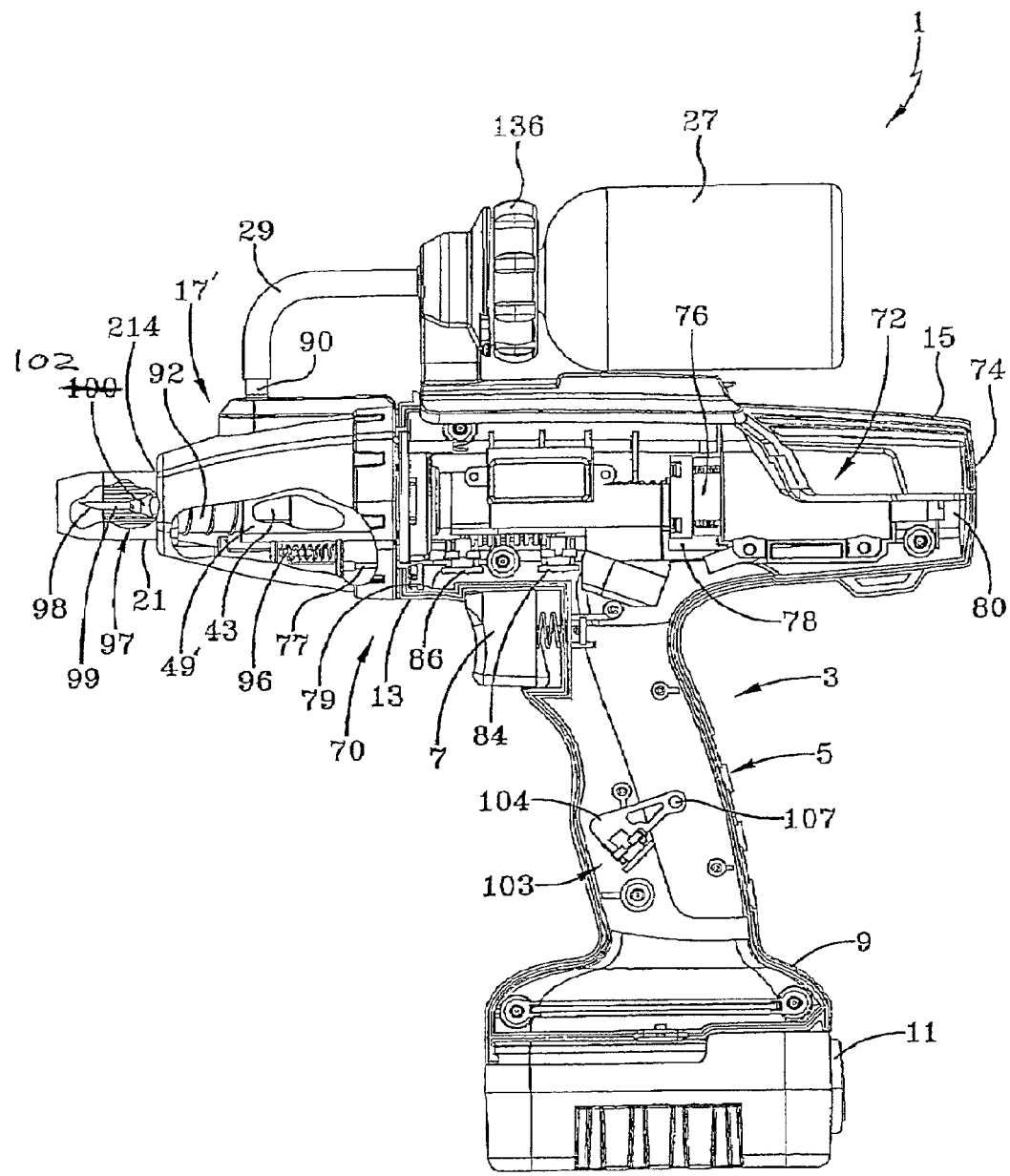
FIG. 4 is a partially cut-away view of the housing revealing the drive assembly and other internal members for the hypodermic injection system.

Referring next to FIG. 3, hypodermic injection system 1 is shown with a detached injection head 17. Extending from a forward end 41 of upper portion 13 is a drive ram or ram device 43 described below. Injection head 17 includes an injection chamber compartment 45 with an injection chamber 49. Injection head 17 has an exterior wall 51 structured to hold injection chamber compartment 45. Injection head 17 and forward end 41 of upper portion 13 are cooperatively configured to enable head 17 to be easily replaced with other injection heads 17 having injection chambers 49 of different sizes. Injection chamber 49 has a specific capacity or volume for holding different maximum quantities of injectate, say 5 cc's, which could be replaced with another injection head 17', as shown in FIG. 3a and FIG. 4, whose injection chamber compartment 49' having a different maximum volume, say 2.5 cc's. The different volumes could be used for different types of injectates, for different animals, for different sizes of animals, different locations on the animal, or people, etc. Volume ranges of 0.25 cc to 2.5 cc and 0.5 cc to 5.0 cc are typical for most animal injections. For very small animals or injectates of certain compounds, a range of 0.025 cc to 0.25 cc would be appropriate. For very large animals and injectates of certain compounds, the range of 1.0 cc to 10.0 cc is appropriate. Further, for very specialized procedures such as plastic surgery or Mesotherapy, very small values at a range of 0.01 cc to 0.05 cc is usually more appropriate. The stroke length of ram 43 can dictate the volume injected. The stroke length of ram 43 for these volumes used with hypodermic injection system 1 will be about 0.1 inch for the lowest volume within a given range and about 1.0 inch for the largest volume within the range. For example, taking an injection head 17 with a range of 1.0 cc to 10.0, ram 43 will travel 0.1 inch to deliver 1.0 cc, and ram 43 will travel 1.0 inch to deliver 10.0 cc. For injection heads for delivering fixed volumes for every injection, the control system will provide the same stroke length for every cycle. Forward end 41 of upper portion 13 has relatively wide access notches (not visible in FIG. 3) for receiving wide ridges 53 of injection head 17, 17' and the rearward end 55 of exterior wall 51 of injection head 17 (or 17', etc.) has an outer ridge 18 for cooperating with a mating surface 20 in upper portion 13 when injection head 17, 17' is connected to upper portion 13 of housing 3. The user can slip the respective ridges 53 on injection head 17 into the corresponding notches on upper portion 13 of housing 3, and then twist head 17 relative to upper portion 13 of housing 3 for a fast insert-and-twist removal for replacement of injection heads 17, 17'. Therein, head 17 is advantageously initially tilted radially for insertion from its final, properly attached position on housing 3 and then twisted to the position shown in FIG. 4. Various other attachment/detachment devices are available and known in the art, including screw and release devices, many sorts of clips and latches, etc. Size indicators 61 are mounted as inserts in support structure 63 on the interior portion of exterior wall 51 of injection head 17. Size indicators 61 indicate the size of the volume of chamber 49 for making an automatic adjustment of a sensing apparatus within housing 3 further discussed below, for making appropriate changes to the control apparatus, also discussed below. Size indicator 61, along with other electrical signal generators, are connected to a microprocessor discussed below. An exit nozzle (which could be a jet exit nozzle comprising an orifice in the forward portion of chamber 49 or the orifice in a perforator assembly attached to the exit path of chamber 49 as discussed below) is located at the forward portion of injection head 17, and a perforator assembly 97 (shown in a cutaway view of nose shield 21 in FIG. 4 as well as a view in FIGS. 7 and 10) if used, is removably seated on a support structure for transferring injectate from an exit nozzle 98 in its perforator shaft 99 extending from a perforator-connecting hub or hub 102 (also illustrated in FIG. 9) to which shaft 99 is permanently attached, into a body receiving an injection. Perforator shaft 99 of perforator assembly 97 is attached to a perforator base 100 which could be a flexible coupling (see FIG. 7a) to prevent damage from sideways torque which may occur from rapid, aggressive animal movement. Perforator hub 102 is advantageously a non-standard Luer end, and is different from that used with standard needles in order to prevent the use of non-authorized penetrating devices on this system, and will attach to a compatible non-standard mating structure on injection head 17 where the hub (not shown) of perforator 97 is inserted as shown in FIG. 4. Exterior wall 51 of injection head 17 is preferably a molded hard plastic such as polycarbonite for a rugged structure in a very difficult agricultural environment, which is the same size for each injection head 17, and variable-sized injection compartments 45 are fixed in place such as by means of an appropriate heat seal, adhesives, press fitting and the like. Nose shield 21 is advantageously made from Delrin® or very slippery polyethylene to resist sticking under the influence of some higher viscosity compounds that are delivered with this system. Size indicators 61 can be made from an appropriate plastic, metal or magnetic material and are inserted into an appropriate holding structure on the interior surface of wall 51, and they are mounted so that it is detectable by an appropriate sensor (such as size sensor 101) at a mating location of upper portion 13. Size indicators 61 are at different locations for injection head 17 with different size chambers, and these cooperate with size sensors 101 having different locations accordingly. Advantageously, size indicator 61 is a magnet and sensor 101 is a Hall magnetic sensor.

Input port 19 comprises a tube with annular flanges for gripping the interior walls of output tube 29 or feed line 31 to hold the latter injectate transfer elements attached to port 19. Port 19 can be integral with housing 51, as can be injection compartment 45.

FIG. 4 shows a drive assembly 70 of hypodermic injection system 1. Drive assembly 70, which is connected and controlled by a microprocessor 272 discussed later, is a direct drive system, meaning that it directly drives drive ram 43, rather than energizing a biasing means such as a spring for imparting energy to drive ram 43 and thereafter having to be re-energized such as by cocking or loading in some other way. Drive assembly 70 incorporates, in the embodiment shown, a ball screw motor assembly 72. Ball screw motor assembly 72, generally very efficient in their transfer of energy, can be one of various types. Ball screw motors include circulating balls which are located in a spiral raceway disposed between a rotating ball screw and an outer nut. As the ball screw is rotated, the balls are driven against adjacent balls for imparting drive force to ram 43, and the balls are fed back to preceding turns. The ball screw can be turned in either direction for driving ram 43 into injection chamber 49 and withdrawing ram 43 from chamber 49, as explained below.

Ball screw motor assembly 72 includes motor 74 having longitudinally extending ball screw 76 and nut 78. Assembly 72 is operatively connected to drive ram 43, and they are located in upper portion 13 of housing 3. A motor heat sink 15 is mounted in direct physical contact with motor 74 for optimizing the transfer of heat from motor 74 to the atmosphere. This feature reduces the likelihood of overheating when making injections at very high rates of speed, such as close to two injections per second, which has been found to occur when used by a highly skilled professional in swine operations. The hypodermic injection system described herein is capable of injecting a 5 cc dose of an injectate in approximately 0.25 to 0.3 seconds, depending on the instant viscosity of the injectate and/or the internal diameter of the exit nozzle. Hence, effective heat dissipation is very important. An internal temperature sensor 80 is positioned to be in direct physical contact with heat sink 15 and motor, 74 which is part of a disabling circuit for disabling hypodermic injector system 1 in case an unsafe, predetermined temperature is reached. Temperature sensor 80 is connected to the microprocessor discussed later.

Finger trigger 7 is electrically connected to a trigger switch 274 (discussed below), which is in turn connected to the microprocessor, discussed later, for controlling motor 74. The actuation of a nose trigger 21 causes a moveable rod 96 with a magnet 77 located inside head, 17, 17' to move closer to forward end 41 where it is magnetically sensed by a Hall sensor 79 to send an actuation signal to a nose switch 276 (FIG. 11). For reasons of safety, the two switches (274, 276) are electrically connected in series; therefore, nose trigger 21 actuation is required at the same time as finger trigger 7 to turn motor 74 on. In some cases, where an additional level of safety is required, a predetermined contact force can be provided in order for either finger switch 7 or nose shield 21 to send an actuator signal to motor 74 energized for an injection. Rearward position detector 84 detects the rearward travel of drive ram 43, and forward position detector 86 detects the forward travel of drive ram 43, by virtue of the engagement thereof by the nut of ball screw 76 which moves to move ram 43. Position detectors 84 and 86 are actuated by the forwardmost and user selected rearward positions, respectively, of drive ram 43 and send electrical signals to the microprocessor, discussed below, to change the direction of rotation of ball screw 76. FIG. 4 shows drive assembly 70 with drive ram 43 in its forwardmost position (to the left in the cut-away view of head 17' in FIG. 4), with an injection just having been given as explained below. Ram 43 is in contact with forward position detector 86 which drive ram 43 has just activated, and ball screw 76 of motor 72 is about to reverse direction as soon as one of the two triggers is released.

An aspect of the operation of hypodermic injection system 1 is as follows. An injection is made when drive ram 43 moves into injection chamber 49 which contains injectate. As ram 43 is driven forward by the balls of ball screw 76, it forces injectate through a properly positioned exit nozzle illustrated as exit nozzle 98 of perforator assembly 97 in FIG. 4. A first one-way or input valve 90, whose direction is shown with an arrow, located in input port 19 (see FIG. 4) allows injectate fluid to flow from the injectate supply through output tube 29 (if bottle 27 is the injectate supply) or feed line 31 (if a remote injectate supply is used) into injection chamber 49 as drive ram 43 is moving outwardly from chamber 49, but allows no flow in the reverse direction when ram 43 is moving into chamber 49 for effecting an injection.

A second one-way or output valve 92, whose direction is also shown with an arrow, is located at exit port 94 located behind nose trigger 21 (discussed below). Second one-way valve 92 allows flow of injectate fluid out of perforator assembly 97 (shown in a cut-away view of nose trigger 21) supported for making an injection, when ram 43 moves in the forward direction into injection chamber 49, but allows no flow (of air or liquid) when ram 43 moves in the reverse direction during the refill cycle when injectate fluid is flowing through port 19, past first one-way valve 90, into chamber 49.

In order to make an injection, a dual trigger arrangement is used to operate hypodermic injection system 1, as mentioned above. Finger trigger 7 is depressed into housing 3 by a user's finger, and nose trigger rod 96 is pushed toward forward end 41 when shield 21 is properly pressed against the injection site, also described above. As explained above, rod 96 is electrically or magnetically sensed by a Hall switch 79 in upper portion 13 which is in turn connected to a nose switch 276 (discussed below) which is in turn connected to microprocessor 272 described later, as is trigger switch 224 to which finger trigger 7 is operatively connected. The depression of finger trigger 7 and nose trigger rod 96 effects the actuation of motor 74, as explained earlier, to energize ball screw 76 to effect movement of drive ram 43. When actuated, movement of nose shield 21 (and in turn, trigger rod 96) also allows perforator shaft 99 to enter the hide, skin, shell or other outer covering of the body to be injected at the injection site. Nose shield 21 (and trigger rod 96) is particularly useful with frisky animals. Since hypodermic injection system 1 as shown in FIG. 4 can only make an injection if nose shield 21 and rod 96 is depressed, the movement of the animal's (or person's) body away from device 1 will immediately stop the injection cycle and operation of system 1 to make an injection. Motor 74 will restart and the injection cycle will continue towards completion as soon as nose trigger rod 96 is again depressed—i.e. as soon as it re-engages the animal or person. This is a major advantage of direct-drive systems over intermediate energy storage springs which have previously been used for supplying injection pressure. To further allow for the continuation of a safe and effective delivery, even though a sudden side-wise movement occurs, perforator-connecting hub 102 alluded to earlier is advantageously installed on flexible coupling 100 discussed above, or a limited movement ball and socket thru-put path.

Still referring to FIG. 4, the injectate supply can be bottle 27 as shown in FIGS. 1, 3 and 4. It is important to prevent air from entering injection chamber 49, therefore, hypodermic injection system 1 incorporates an orientation switch assembly 103 which requires that system 1 be pointed in the downward direction during the injectate refill portion of the cycle to prevent the pulling of air into injection chamber 49 when bottle 27 is approaching the empty condition, i.e., the fluid input path of a septum spike 128 (FIG. 6) discussed later, is not covered with fluid. Orientation switch assembly 103 incorporates an orientation switch pendulum 104 mounted on a pivot pin 107 extending from housing 3, and a refill switch discussed below, which is connected to microprocessor 272 explained later, for controlling the operation of motor 74. With bottle 27 properly installed on housing 3, and after an injection has been made and the user wants to refill injection chamber 49, housing 3 is tipped downwardly. Pendulum 104 remains in its vertical position, and when housing 3 is tipped far enough to a refill actuation position, pendulum 104 actuates the refill switch to effect the withdrawal of drive ram 43 from injection chamber 49 in injection head 17. Injectate fluid flows from the bottle 27 through input port 19, past first input valve 90 and into chamber 49. Orientation switch assembly 103 is disabled with an appropriate command is entered on control panel 25 when bottle 27 is not used as the injectate supply and a remote supply provides the injectate. It is further noted that maintaining the downward position of housing 3 will allow for the rapid injection rate alluded to earlier, for example, when injecting pigs, all of which have been moved to a shoulder to shoulder position in pens, and located at a lower level than that of the operator.

The correct amount of reverse movement of drive ram 43 during the refill cycle is controlled by an internal switching mechanism that is user selected. This assures that the correct volume is pulled into injection chamber 49. The device for selecting the correct location for placing the volume control sensors can be done by means of a magnetic coupling to move a mechanical or optical switch, or alternatively, counting shaft rotations of the motor if a waterproof structure is needed or by moving it through an open slot if a sealed unit is not required. In the embodiment shown, shaft rotations are counted by the movement of the ball screw nut (not shown), with an optical sensor.

Hypodermic injection system 1 is powered by a storage battery 11. Storage battery 11 is mechanically attached to base 9 by a clamping mechanism of many possible types, including guide rails on one of the bottom of base 9 and the top of battery 11, or vice versa, and base 9 and battery 11 could each have cooperating rails and channels, which could be dovetailed shaped to prevent accidental release. Battery 11 is electrically connected to the electronic circuitry in system 1 when battery 11 is properly installed. Battery 11 can easily be removed for replacement and can be recharged either when removed from housing 3 or while installed thereon. As noted above and described below, a low voltage warning arrangement is provided to advise when battery 11 should be replaced.

Figure 5:
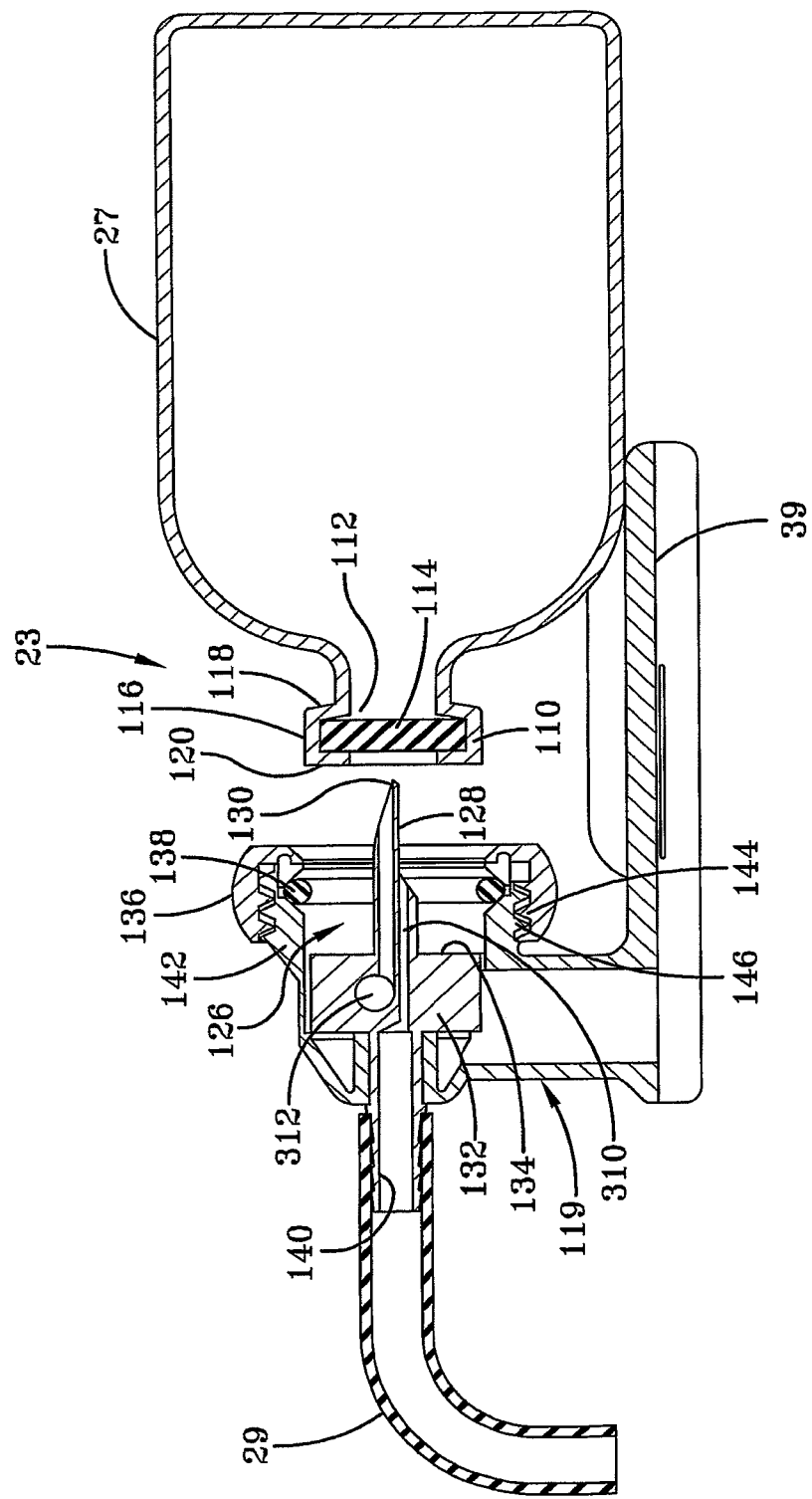
FIG. 5 is a partially cut-away side view of a bottle mounting carriage assembly and a bottle prior to the operative connection of the bottle to the hypodermic injection system.
Figure 6:
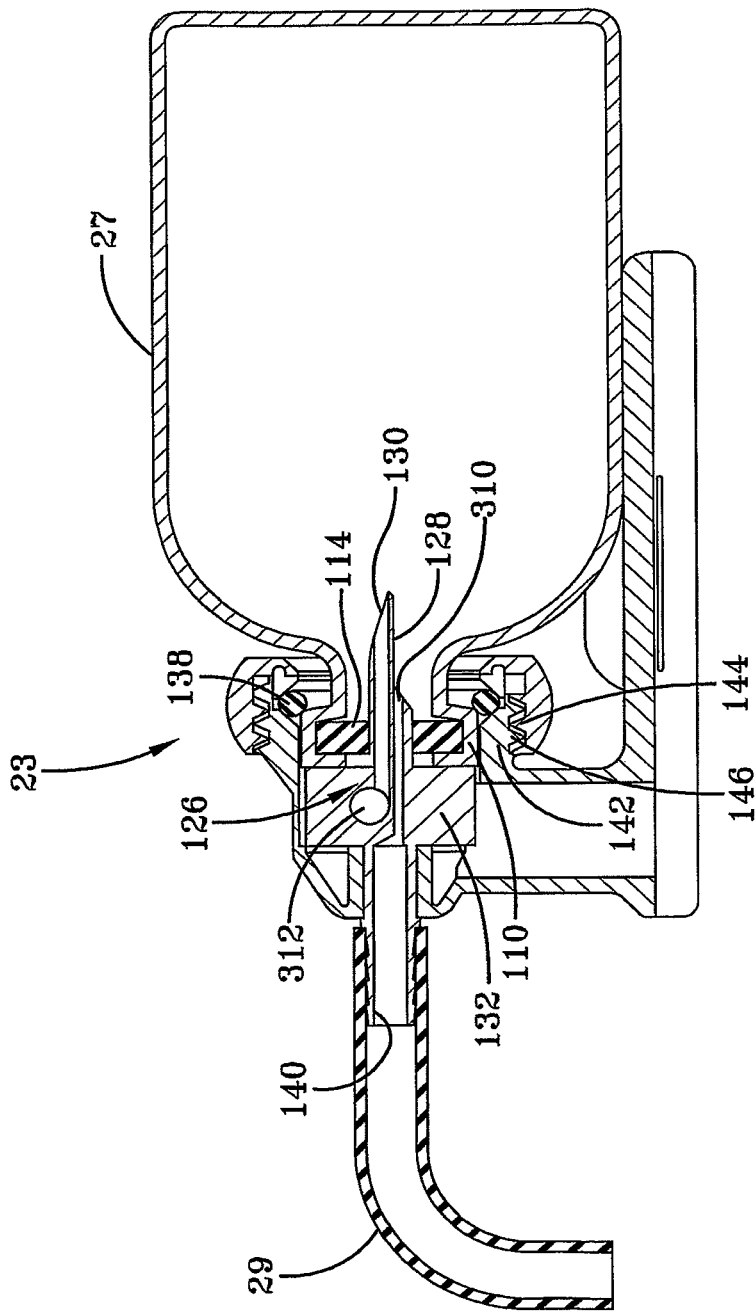
FIG. 6 is a partially cut-away side view of the bottle mounting carriage assembly shown in FIG. 5 with the bottle in the operative connection to the hypodermic injection system.

Turning next to FIGS. 5 and 6, bottle 27 and bottle mounting carriage assembly 23 are shown. FIG. 5 shows bottle 27 prior to its being inserted for the injection procedure, and FIG. 6 shows bottle 27 securely connected to a bottle mounting carriage. Bottle 27 includes a hub 110 defining an opening 112 across which is a rubber or rubber-like septum 114 which is shown in an unpierced state in FIG. 5. Hub 110 has a hub side 116, an annular rear shoulder 118 and a front rim 120. Carriage assembly 23 has base 39 which is secured to housing 3 and includes an upstanding arm 119 mentioned earlier. A bottle spike assembly 126 includes a septum spike 128, with an atmospheric air passage 312, and which is hollow and has an inclined point 130 for piercing septum 114. Spike assembly 126 further includes a bottle support area 132 through which septum spike 128 extends, and hub support 132 has a flat surface 134 against which rim 120 can be seated. An annular locking knob 136 (see also FIG. 4) surrounds the periphery of support area 132, and an O-ring 138 is disposed inwardly of locking knob 136 and around septum spike 128. An outlet port 140 extends forwardly from spike assembly 126 for receiving injectate flow passing through a fluid flow path 310 of septum spike 128. Output tube 29 is attached to port 140, and its free end is provided for attachment to input port 19 of injection head 17.

In order to install bottle 27 in carriage assembly 23, bottle 27 is placed in the proper position on base 39 as shown in FIG. 5. Bottle 27 is then moved towards spike 128, which pierces septum 114 and rim 120 is moved towards engagement with surface 134. As hub 110 moves past O-ring 138, O-ring 138 grips shoulder 118 of bottle 27, which is gripped by locking knob 136 of which O-ring 138 forms a part. O-ring 138 is compressed as hub 110 passes through it. Locking knob 136 tightens O-ring 138 against hub 110 to apply a radial squeezing force on O-ring 138 to hold bottle 27 securely in place.

In order to remove bottle 27 from carriage assembly 23, locking knob 136 is turned to loosen it, and bottle 27 is then pulled away from carriage assembly 23. This device is easy to use, and O-rings 138 can easily be replaced if they are worn or damaged. Locking knob 136 cooperates with a knob support structure 142, and they have bayonet threads 144 and 146, respectively, so that tightening can easily be accomplished by the turning of knob 136. Carriage assembly 23 has an additional advantage in that it provides support to bottle 27 for enabling bottle 27 and carriage assembly 23 to withstand many impacts without breaking or opening the seal between rubber septum 114 and septum spike 128.

Figure 7A:
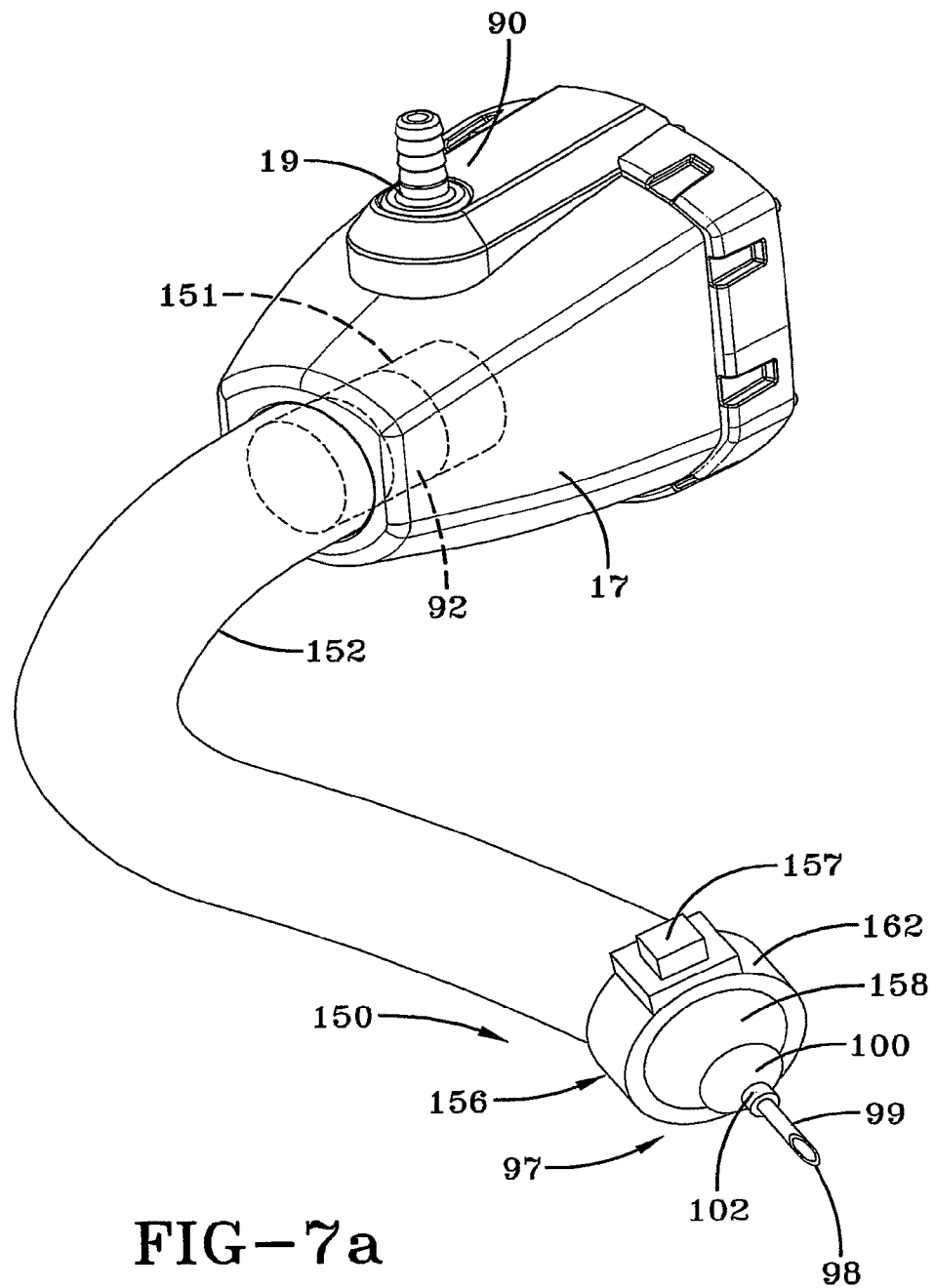
FIG. 7a is a perspective view of an injection head of the hypodermic injection system shown in FIG. 1 with an extension tube to a remote injection nozzle and trigger assembly, with internal parts shown in phantom.

FIG. 7a shows injection head 17 connected to which is a remote injection and control device 150. Injection head 17 has input port 19 as discussed earlier, and inside which is located input one-way valve 90, also discussed earlier. An extension tube 152 has at one end an attachment configuration for sliding over an appropriate tube support structure 151 shown in phantom and inside which is output one-way valve 92. Extension tube 152 is a flexible, hygienic tube made of an appropriate flexible rubber, plastic or fabric like product, and is connected at its free end to a remote hand-held injection nozzle assembly or remote handpiece 156. Nozzle assembly 156 includes a perforator holding structure 158 for releasably holding perforator assembly 97 whose perforator exit nozzle 98 is shown. Perforator holding structure 158 is affixed to extension tube 152 by means of a collar 162 which wraps around the free end of extension tube 152 and to which remote nozzle assembly 156 extends. An operator-actuated injection trigger 157 is mounted for operating hypodermic injection system 1 at a distance remote from housing 3. Trigger 157 and assembly 156 send an appropriate signal to microprocessor 272 discussed below, to operate a drive system switch discussed below for actuating motor 74 to provoke an injection. Everything works just as earlier described for injection head 17, ram 43, and input valve 90 and output 92, with the exception of the fact that the entire length of tube 152 contains injectate (rather than just chamber 49) which is progressively delivered into the injection site at the selected volume. In the remote hand-piece embodiment, finger trigger 7 is not easily assessable to the user and is therefore configured to be permanently activated when remote device 150 is attached, that is, only switch 157 is required to operate motor 74. The signal from remote switch 157 could be one of many different types, including a radio frequency signal, an optical signal, a hard-wired signal using lines leading from assembly 156 back to the switch, a hydraulic signal, and the like, and although it is not shown as such in FIG. 7a, it could also be a nose trigger like nose trigger 21. The remote nozzle assembly 156 provides for greater user flexibility in tight situations, and is particularly useful for injecting marine life, such as crustaceans and fish, where careful location of the injection is very important. The remote system permits easy implementation and enables the operator to use both hands when bringing the animal to the remote hand-held injection nozzle assembly 156, which is located on a fixture of one sort or another, rather than bringing the injection system to the animal. Bringing the animal directly to injection system 1 mounted on an appropriate fixture is, of course, also possible, however, the smaller remote embodiment shown makes it easier for limited space situations.

Figures 7B, 7C:
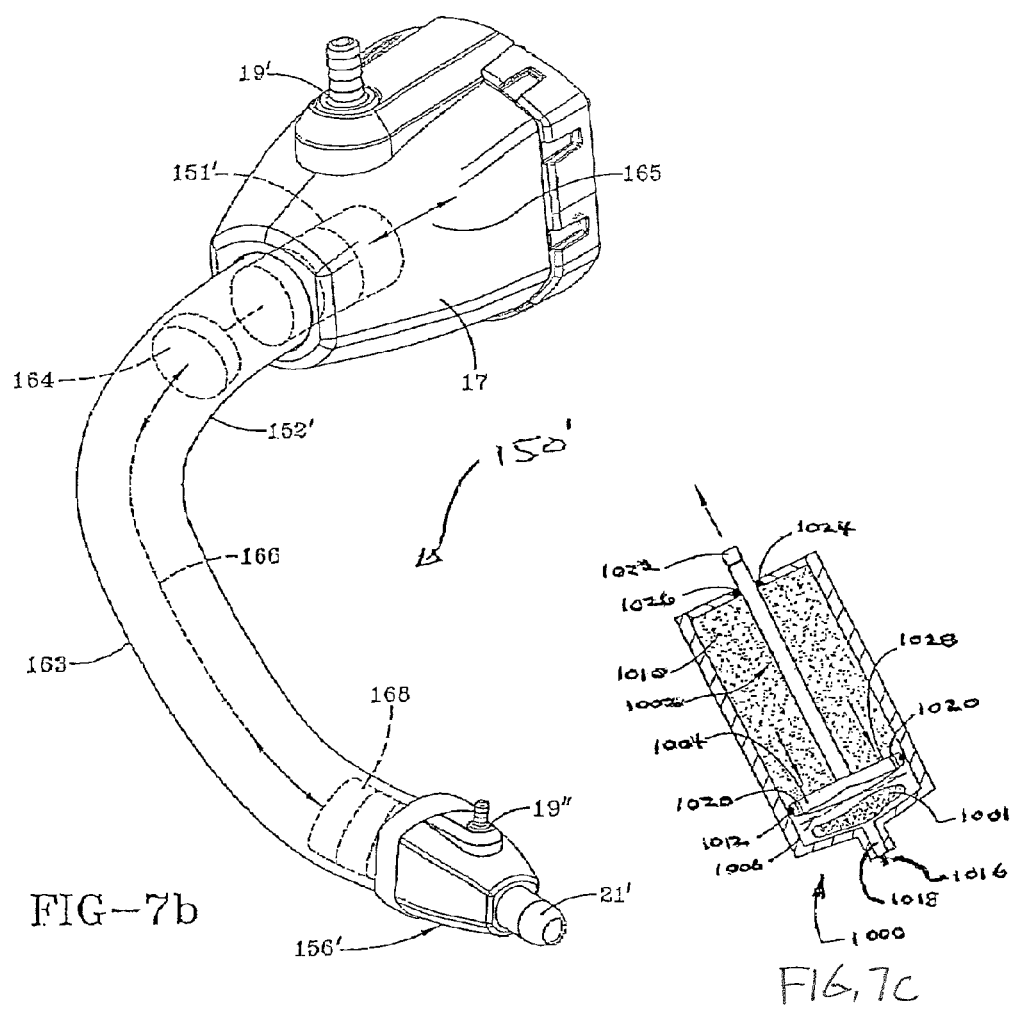
FIG. 7b is a perspective view, similar to that shown in FIG. 7a, having a hydraulic coupling tube.

FIG. 7b, illustrates a connecting operating cable or tube 163 to a remote handpiece 156'. Cable 163 is a hydraulic coupling tube filled with fluid, and having two pistons, a rearward piston 164 at the main housing, and a forward piston 168 at remote handpiece 156', and having an inner light-weight mechanical connection 166 between the pistons 164, 168. To give an injection, ram 43 (shown in FIG. 3) moves forward and pushes rearward piston 164 forward as well, and of course, forward piston 168 goes forward by the same amount because the fluid in tube 163 is incompressible. Pulling back on a rear piston 164 with ram 43 to reload also pulls back forward piston 168 at the remote location because of connecting cable 166. For this embodiment, remote handpiece 156' operates the same way as injection head 17 did for the earlier description, that is, the fluid is drawn into port 19' and injected through an exit nozzle within shield 21'. The same action/reaction can be achieved with a two part mechanical cable, one part being moveable and the second part being stationary. The latter cable can operate in a push/pull mode, or alternatively, rotating a screw assembly at remote handpiece 156' can also transfer the energy needed to provide injection energy at remote handpiece 156' Finally, as with the main housing capability, remote handpiece 156' can be adapted to take replaceable multi-shot cartridges where the injectate is delivered in small steps with the jog feature of the control system as described below, or alternatively, single-shot cartridges, and as described below, the volume touch-pad control would tell the injection system how far to pull back ram 43 for the volume to be delivered.

Referring to FIG. 7C, the concept of remote handpiece 156' accepting replaceable cartridges (Discussed again below) is shown with an accompanying illustration in FIG. 7b. In this regard, FIG. 7b discloses a remote ampule 1000 containing lyophilized vaccine 1001 and its diluent 1010, the two being separated by a piston 1002 having a piston head 1004 with a one-way valve 1006 in the direction of an exit nozzle 1018. With this embodiment, umbrella valve 1006 will open (as shown in dotted lines) when piston 1002 is pulled back in the direction of the arrow, wherein a diluent 1010 is forced through the fluid flow path channel, past the one way valve 1006 and into the lyophilized portion of the chamber for immediate mixing. Piston 1002 has a ring seal 1012 for sealing against fluid flow around the periphery of piston 1002. The injection or series of injections into the Subcutaneous, Intramuscular or Intradermal regions as the case may be, is given by first slightly advancing piston 1012 to expel any air through now sealed umbrella valve 1006 and its throughput ports 1020. When ready, continuing to push piston 1002 forward will deliver the required injection(s). A one way valve 1016 shown at exit port 1018 is needed to prevent air from being pulled into ampule 1000 when piston 1002 is withdrawn during the mixing operation but will permit the exit of air and thereafter the injection fluid. Piston rod 1022 has a groove at its endpoint which is grasped by a mating structure on piston 168 when motor reversal provokes the mixing action. A seal 1024 is provided to prevent leakage through orifice 1026 as piston 1002 moves in either direction. Alternatively, the grasping groove on the end of rod 1022 can be replaced by a magnetic coupling. The cartridges can be made to self-destruct at the end of an injection to avoid the possibility of reusing them. Such self-destructive cartridges are disclosed, for example, in U.S. Pat. No. 6,056,716 and US Publication No. US2003/0040715A1.

Figure 8:
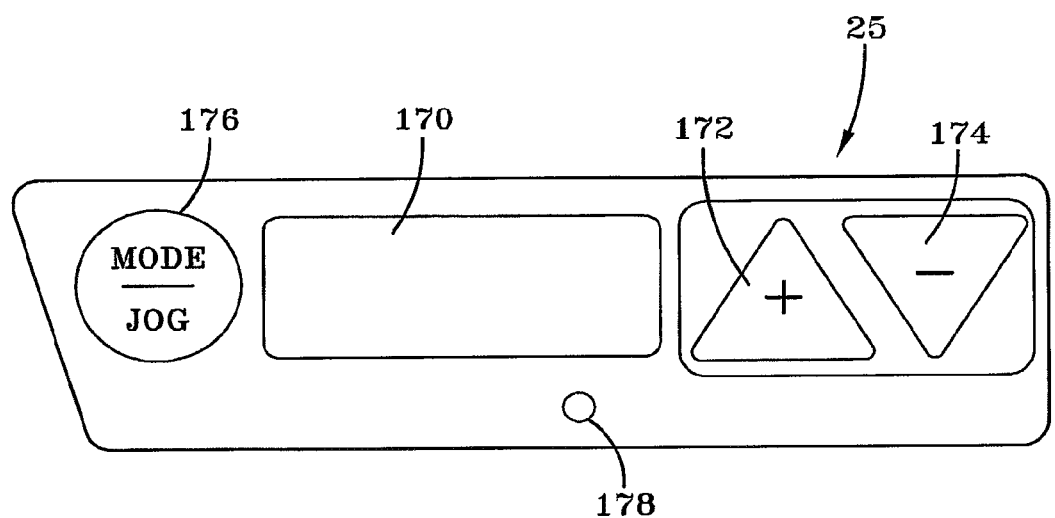
FIG. 8 is a front view of the control and display panel of the hypodermic injection system shown in FIG. 1.

Control and control display 25 is shown in enlarged form in FIG. 8. Control and control display 25 includes an optical display 170 which shows all of the vital parameters for operation of hypodermic injection system 1. Control and control display 25 further includes plus and minus control buttons 172, 174 for increasing or decreasing the selected injection volume for any of the several injection heads 17 which are operatively attached to housing 3. The mode portion of mode/jog button 176 provides for showing four functions on the display and/or for operation of the injector. The first function indicates to the operator which of injection heads 17, having different sizes of injection chambers 49, is attached to housing 3. The second function displays the volume setting selected with the plus and minus buttons 172, 174. The third function enables the operator to switch injection system 1 between bottle-feed from bottle 27 or line-feed from an injectate reservoir for either engaging or disengaging orientation switch assembly 103. Finally, the fourth function of mode/jog button 176 switches display 170 between the non-resettable life cycle count and the resettable session count. The life cycle counter records the total number of injections made since the particular injection system 1 was manufactured, whereas the resettable session counter visually advises the operator how many injections were given by the particular hypodermic injection system 1 during a particular period of time, in a particular location (such as a barn or clinic), by a particular person or the like. These counters are like the odometer in an automobile, and the resettable count is cleared to zero by simultaneously depressing the plus and minus buttons for approximately 3 seconds.

The jog portion of mode/jog button 176 becomes active if this button is depressed for about three seconds, and is used when a new supply of injectate is connected to input port 19 of injection head 17. A new supply of injectate fluid usually pulls some air into injection chamber 49 when the first supply of injectate fluid is pulled into chamber 49. The air must be removed before proceeding. Air removal is facilitated by first holding the button down for the required amount of time, and then pointing injection system 1 in the upward direction so that any air space will move toward nozzle 98 or whatever nozzle exists. If mode/jog button 176 continues to be held in the on position and finger trigger 7 is repeatedly depressed, this repeated depression of trigger 7 causes drive ram 43 to advance in very small steps, each of which expels some of the air from injection chamber 49. As soon as all of the air is removed and ram 43 engages nothing but the remaining injectate fluid in injection chamber 49, the jog button is released and motor 72 is immediately reversed and drive ram 43 returns to its home or refill position. The suction created by pulling drive ram 43 in the rearward direction will only draw injectate fluid into chamber 49 at this time, and the injection procedure can safely continue.

Control and control display 25 has a display port 178 which is advantageously a two-color LED. The purpose of display port 178 is to advise the user of one of three things, according to the following color code. First, if display port 178 is green, all injection functions are working. Second, if display port 178 is solid red, a motor-overload and/or low battery voltage condition exists. Overload is usually caused by excessive current being drawn by motor 72, as well as a short circuit. Motor overload sometimes occurs when injection nozzle 98 (or whatever nozzle is in place) is clogged or otherwise comes up against a bone or very dense tissue at the injection site. Finally, when display port 178 is blinking, a low, but nevertheless functional, battery condition exists. Of course, many other devices for yielding the foregoing signals are possible.

All of the components of control and control display 25 are operatively connected to microprocessor 272, discussed below. These include display 170, buttons 172, 174 and 176, and display port 178.

Figure 9A:
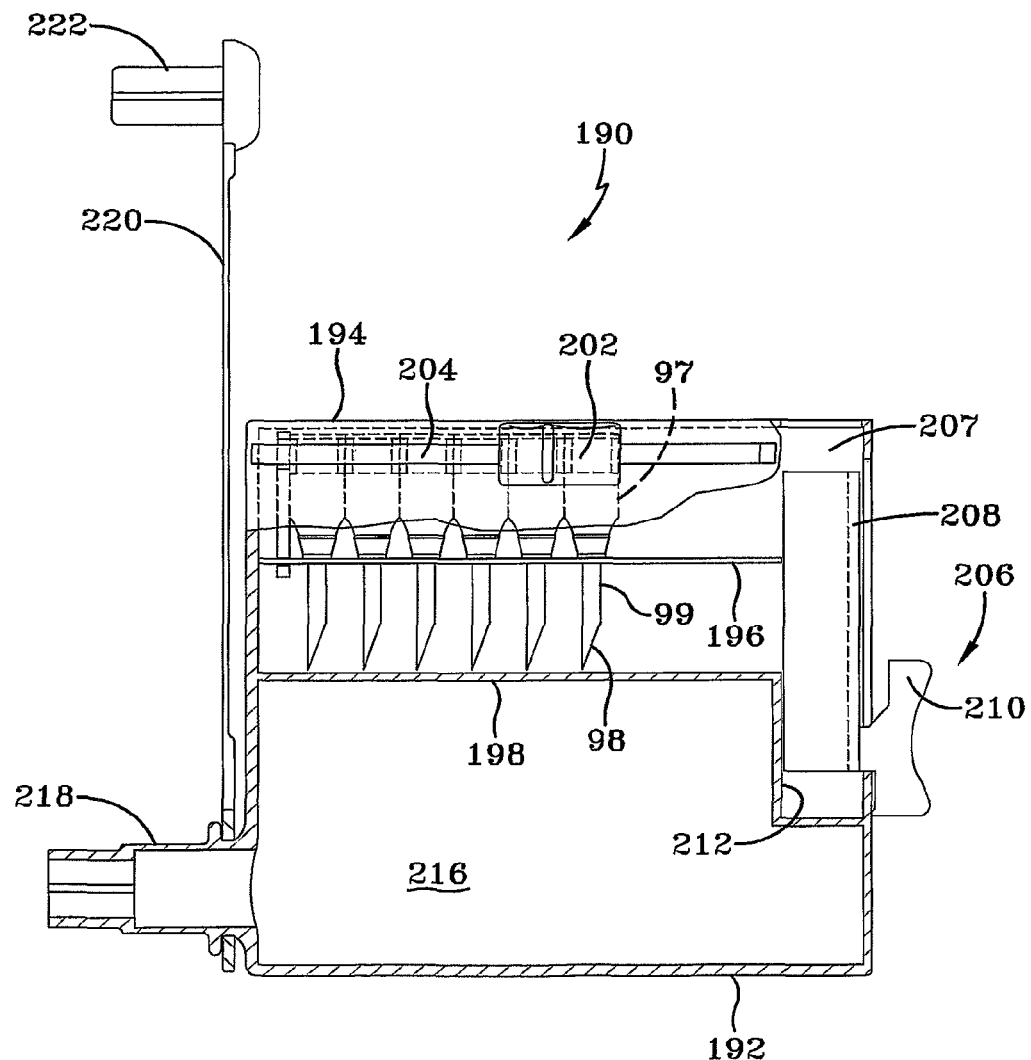
FIG. 9a is a perspective, partially cut-away view of a magazine-holding perforator assembly disposed in a carriage assembly in a condition for loading a perforator assembly in an injection head.
Figure 9B:
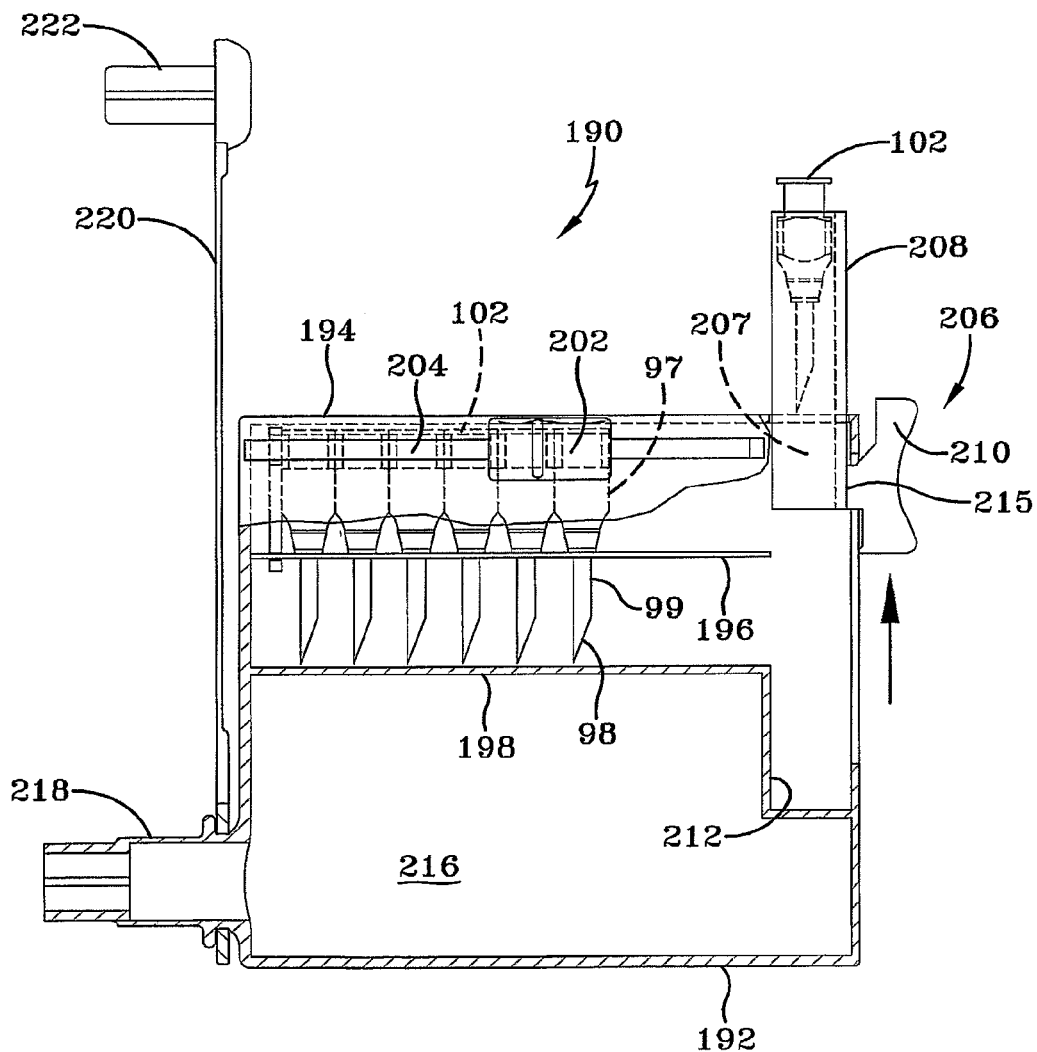
FIG. 9b is a perspective, partially cut-away view of the magazine with perforator assemblies loaded in the carriage assembly shown in FIG. 9a in the process of advancing and securing a perforator assembly to the injection head.
Figure 9C:
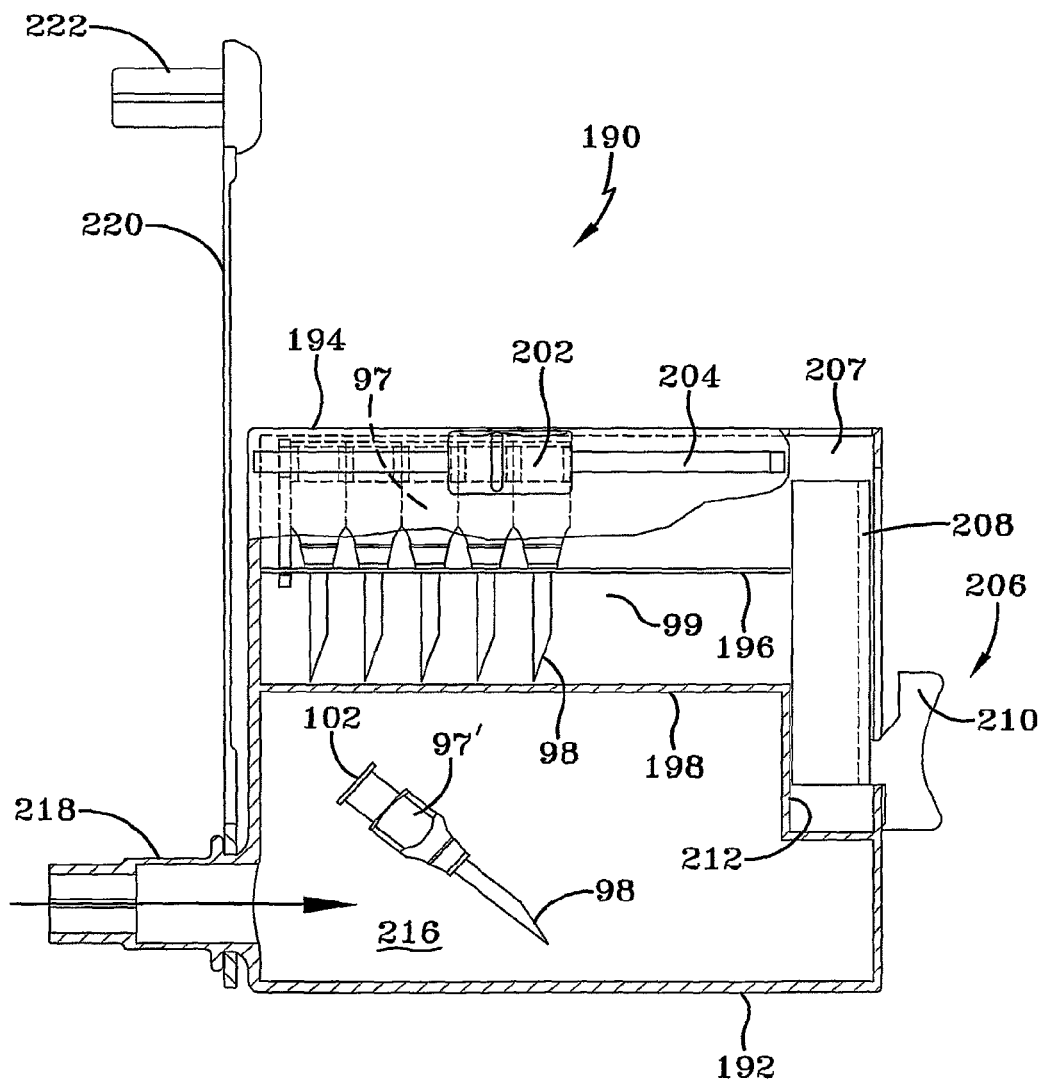
FIG. 9c is a perspective, partially cut-away view of the magazine with perforator assemblies loaded in the carriage assembly depicted in FIG. 9a with a used perforator assembly safely contained and stored in a holding chamber.

FIGS. 9a, 9b and 9c each show a magazine 190 for holding new or fresh perforator assemblies 97 having perforator hubs 102 and for receiving spent or used perforator assemblies 97'. Magazine 190 includes an outer magazine housing 192 having upper guide walls 194 for guiding one or more perforator assemblies 97 as in magazine 190, an upper slotted shelf 196 for receiving the upper ends of perforator assemblies 97 with perforator shafts 99 extending therethrough, and a lower shelf 198 near which the exit nozzles 98 of perforator shaft 99 are disposed. A slider 202 extends through a slot 204 of magazine 190 and is configured to slide perforator assemblies 97 towards a transport assembly 206. Transport assembly 206 includes a lift 208 with a handle 210, a shaft 212 for guiding lift 208, and slot 215 for guiding handle 210. Slot 202 engages perforator assembly 97 closest to lift 208 and moves it towards lift 208, as shown at rest in FIG. 9a, into lift 208. Handle 210 raises lift 208 with a perforator assembly disposed therein as shown in FIG. 9b. FIG. 9b shows hub Luer end 102 extending upwardly from lift 208. Still referring to FIG. 9b, magazine 190 serves as a tool for properly mounting perforator assembly 97 in injection head 17. Injection head 17 has a Luer lock 214 (FIG. 4) which can be one of many known in the art, modified according to the configuration of hub 102 on perforator assembly 97. The user takes magazine 190 and uses it to insert Luer end 102 of perforator assembly 97 extending from lift 208 into the nose end of injection head 17, and twists magazine 190 to lock Luer end 102 and perforator assembly 97 in place on Luer lock 214. This assures the firm securing of perforator assembly 97 in injection head 17 and prevents inadvertent ejection of an improperly connected perforator assembly.

Magazine 190 has a spent perforator chamber 216 and a spent perforator port 218 extending therefrom. In order to remove a spent perforator assembly 97' from injection head 17, the user slides port 208 over the perforator assembly 97' extending from injection head 17 and twists magazine 190 in the opposite direction to that for installation to withdraw perforator assembly 97' from injection head 17. Luer end 102 of the spent perforator assembly 97' would be partially extending outwardly from port 208. Magazine 190 incorporates a flexible arm 220 extending along the same side of magazine 190 where used perforator access port 218 is located, and flexible arm 218 includes an insertion device or protrusion 222 extending therefrom and being parallel to port 218 when in the rest position. Once perforator assembly 97 has been removed from port 208, exit nozzle end 98 is inserted in port 218, and arm 220 is bent over about 180.degree. and protrusion 222 is pushed against Luer end 102 of perforator assembly 97' to push perforator assembly 97' into receptacle 216. Spent perforator assembly 97' is thus inaccessible and safe to the user. Arm 220 can be configured to have protrusion 222 on flexible arm 220 go to port 208 and grasp the used perforator so that no contact by the user is needed. It will then be moved to port 218 and discarded as described above.

In order to assure the proper tightening of perforator assembly 97 in injection head 17, a ratchet arrangement can be used. In this situation, magazine 190 inserts the Luer end 102 of perforator assembly 97 into Luer lock 214 of injection head 17, and magazine 190 is then twisted around the longitudinal axis of perforator assembly 97 until the ratchet assembly starts slipping. The ratchet assembly has been set to start slipping when the torque has been reached assuring perforator assembly 97 has been properly tightened. Therefore, when the ratchet assembly starts slipping, perforator assembly 97 has been properly tightened and installed in injection head 17.

Figure 10:
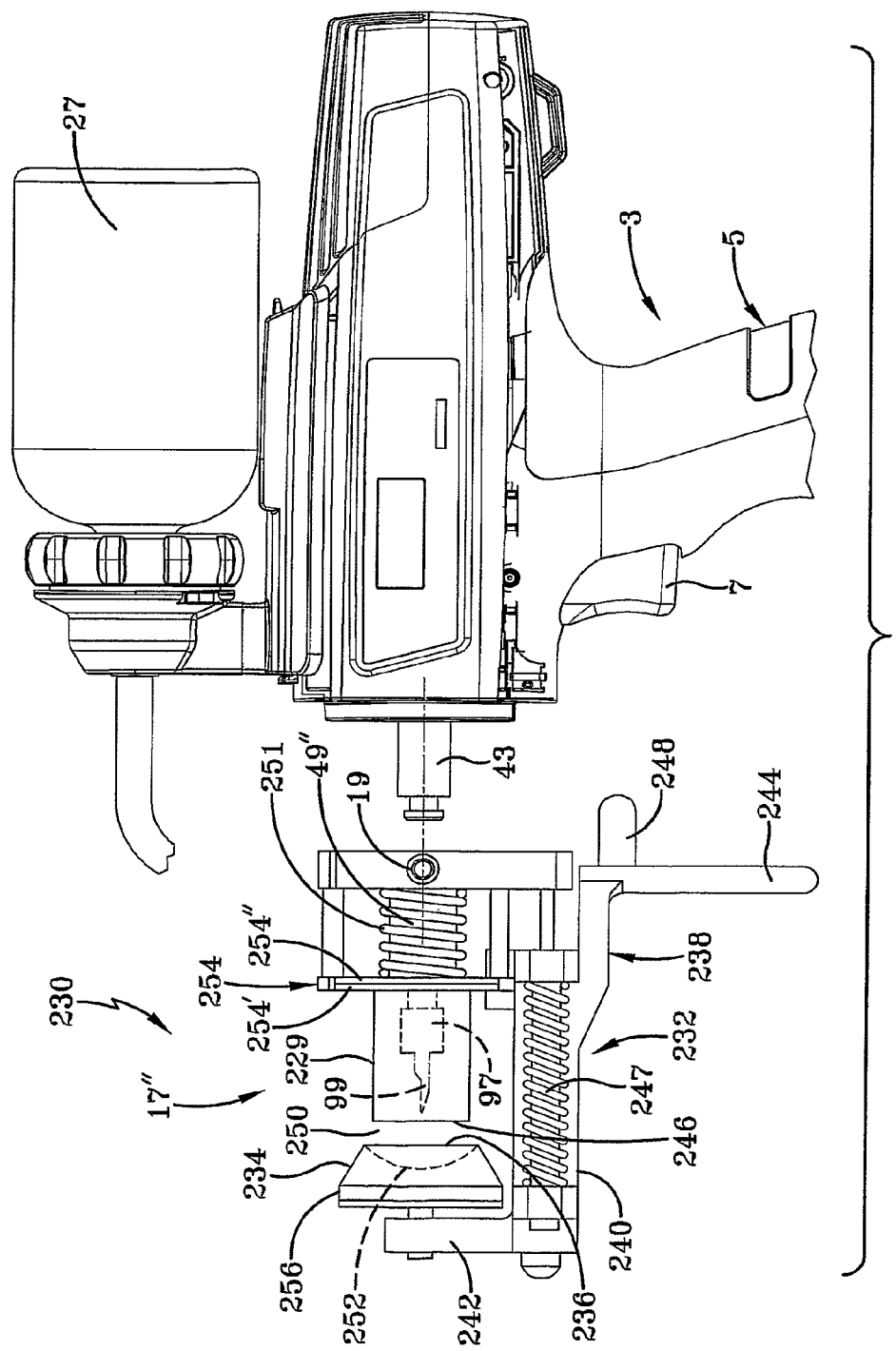
FIG. 10 is a side view of the hypodermic injection system shown in FIG. 1 with a partly exploded view of an injection site clamp assembly on the system.

FIG. 10 shows injection system 1 holding a bottle 27, an alternative injection head 17" having a nose shield 229, and an input port 19, all as discussed earlier. Also shown in FIG. 10 is a clamp assembly 230 for use with a loose body part such as loose skin, an ear, a turkey wattle or the like of an animal or person. Clamp assembly 230 includes an appropriate attachment assembly 232 for operatively attaching clamp assembly 230 to configure an interface connection to upper portion 13 in the same manner as injection head 17 as previously described, a movable clamping pad 234 with a clamping surface 236 and being supported on a movable support 238. Support 238 comprises an elongated arm 240 with a support column 242 supporting pad 234, and a handle 244 for moving pad 234. An opposed clamping surfaces 246 is disposed on nose shield 229, and surfaces 236 and 246 hold the body part to be injected. A spring 247 biases pad 234 to the open or unclamped position. A handle extension 248 extends rearwardly from handle 244 and is in line with trigger 7.

In order to operate clamp assembly 230, the operator moves handle 244 towards trigger 7 to open a gap 250 (by virtue of a cam arrangement or the like), between clamping surfaces 236 and 246. The operator then slides the body part into which an injection is to be made into gap 250. This could include the skin of an animal, such as the skin on the neck of a cow, an ear such as the ear of a pig, a wattle of a turkey, and the like. A spring 251 biases nose shield 229 to the forward position to hide perforator assembly 97. Until this occurs, spring 247 has had no effect. The user then continues to pull handle 244 towards trigger 7 of housing 3 against the bias of spring 251 until shield 229 moves inward (similar to nose shield 21) thus allowing perforator assembly 97 to enter the injection site, and at this time, trigger actuator 248 actuates finger trigger 7 for effecting the injection. At the same time that the bias of spring 251 is overcome, so also is the bias of spring 247. Perforator assembly 97 effects the injection, and pad 234, whose clamping surface 236 is soft and pliable, yields and distorts under the balloon-like effect due to back pressure as the injectate enters the tissue of the body portion being injected. The distortion of clamping surface 236 is shown in dotted lines 252. Perforator 97 enters only one surface of the skin and does not pass through two surfaces such as the two surfaces of animal skin disposed in gap 250, a turkey wattle 250, and the like. The yielding action of pad 234 provides the space needed for the injectate to enter the body being injected, and at the same time urges rapid distribution of the fluid injectate away from the site of the puncture caused by perforator 97. The distribution of the injectate upon injection substantially eliminates the likelihood of the injectate coming back out of the entry hole in the body; however, to even further discourage the possibility of leak-back, surface 246 can include a second foam surface through which perforator assembly 97 will emerge as it enters the injection site. Not only will this second foam surface provide even more room for the heretofore described ballooning effect while encouraging the injectate to spread out, but it also serves to seal the puncture hole when perforator assembly 97 is withdrawn. This short lived surface contact of the foam and the puncture hole will end when clamp assembly 230 opens and is removed from the body part, but will last long enough to fully discourage leak-back of the injectate. While a little more complicated, a shutter like assembly that opens when perforator 97 advances, and closes at withdrawal, will also momentarily seal the entry hole to discourage leak-back. Finally, while not heretofore mentioned, nose shield 21 can also utilize a foam contact surface to discourage leak-back when working with thin skinned animals such as very young piglets and the like.

At the end of the injection process in which injectate is delivered into a body, and as the injectate spreads out in the body, the pliable material of clamping pad 240 returns to its initial shape. This is a very important feature since the thickness of pad 234, and its diameter and durometer, are provided for each particular type of animal or person being injected, and the selected injection site. When handle 244 is released, so is pad 234 as clamp assembly 230 opens under the influence of spring 247 to remove perforator assembly 97 from the injection site, and as surfaces 236 and 246 separate to provide for easy removal of the body part and then a return to the closed position, which is the rest state. Spring 251 returns nose shield 229 to its rest position to hide perforator assembly 97.

Apparatus is provided for enabling clamp assembly 230 to pivot about a plane going through a door 254. Door 254 is a disc-like structure having two mating halves 254' and 254". A hinge is mounted on both halves 254' and 254" on the opposite side of the view shown in FIG. 10. Door half 254' can pivot 90.degree. clockwise when viewed from the top. This swinging open of door 254 of clamp assembly 230 allows for a view of a modified injection chamber 49" and more importantly provides a spring-loaded pocket or receptacle 256 for perforator assembly 97 to be safely inserted and removed from injection head 17". Pocket 256 further exerts the force needed to secure perforator assembly 97 in place when clamp assembly 230 is closed and provides for easy removal of perforator assembly 97 when opened. This feature allows use of the far less expensive force-fit of a plastic perforator hub rather than the more expensive metal-type twist-on Luer lock known in the art. However, in either case, the interface between the perforator hub and its connection to the injector will use the custom characteristics described earlier to prevent the use of unauthorized standard needle assemblies and the risks that that go with it.

If door halves 254' and 254" of clamp assembly 230 fail to properly close after they have been swung open, for either a change of perforator assembly 97 or for the visual inspection of injection chamber 49", the injection capability of injection system 1 is disabled because nose shield 229 does not line up over injection chamber 49". Furthermore, any other defect, operator error or some impediment to the normal operation of clamping assembly 230 will disable hypodermic injection system 1 through electronic means by preventing the trigger actions as described earlier, to further insure the safety of system 1.

As noted above, perforator shaft 99 is long enough to penetrate one side of the folded or tented skin folds of a cow or other animal but not the other side, wherefore the injectate is readily deposited in the subcutaneous space just below the inside layer of the skin, thus totally avoiding any possible damage to the muscle of the animal. Also as noted above, injectate may occasionally flow back out of the injection site. This is more likely to happen in the ear because there is no soft, pliable region characterized with the muscle. However, leak-back is virtually eliminated when using a perforator shaft 99 whose length penetrates the ear cartilage but does not come out of the other side. Injectate injected into an ear is delivered to the subcutaneous space on the opposite side of the cartridge where the injection was given, wherein the injectate has a hard time coming back through the small hole in the ear especially if soft pad 234 and a mating pad at location 246 are used on the outside surfaces for urging the injectate to spread out after an injection is made.

Turning next to FIG. 11, shown in block form is the electrical connection of the components of an electronic system 270 incorporated in hypodermic injection system 1. The system is connected to a microprocessor 272 which electronically controls system 1. Microprocessor 272 uses a series of input signals from properly located switches, discussed above, and its sensors, also discussed above, to generate all electrical signals for controlling the functions of hypodermic injection system 1. The switches connected to microprocessor 272 are a trigger switch 274 which is actuated by trigger 7, a nose switch 276 which is actuated by nose shield 21, or shield 229 when using clamp 230, a home switch 278 actuable by forward position detector 86, which signals processor 272 that drive ram 43 has reached its full-forward position after all of the injectate has been delivered into the injection site. Dose-measuring switch 280 determines the dose volume of injectate being injected and determines how far in the reverse direction to draw the selected amount of injectate into injection chamber 49. The position of dose-measuring switch 280 is selected by the operator by pushing plus and minus control buttons 172 and 174.

The orientation of injector system 1 when a new volume of injectate is pulled into injection chamber 49 is sensed by orientation switch assembly 103 which actuates a tilt switch 282, which is in turn electrically connected to microprocessor 272. As explained earlier, the orientation of hypodermic injection system 1 is very important to insure that only injectate, and no air, is drawn into chamber 49 when operating in the bottle-feed mode. As also explained earlier, the mode of operation of hypodermic injection system 1 is indicated with mode/jog button 176 on control and control display 25.

Also as discussed earlier, any number of injection heads 17, 17' can be attached to housing 3. An injection head switch 284 can tell the difference between different volumes of heads, as shown in FIGS. 3 and 3a, such as 2.5 cc or 5.0 cc heads. When a particular head is detected, display 170 shows an appropriate volume range for that head. In some cases, a head configured to deliver a fixed volume for every shot is required. One such application is for the smaller volumes delivered with dermal vaccines, which could be in the order of 0.2 to 0.5 cc, or perhaps certain procedures in plastic surgery or Mesotherapy where the volume range may be in the order of 0.01 to 0.05 cc. In these cases, injection head switch 284 would control injection system 1 to deliver the correct volume.

Motor temperature is measured by internal temperature sensor 80, which is also connected to microprocessor 272. As explained earlier, a disabling circuit in microprocessor 272 will terminate drive signals to motor 74, which is a very important safety precaution for preventing damage to the motor, to therefore provide motor 74 with a long life and assure that it will continue to deliver injections at the specified speed.

Also as explained earlier, injection system 1 can measure two count values. A count memory 286 stores count values. One of the count values is the non-reset life-cycle count for measuring the total number of injections made from the time hypodermic injection system 1 is assembled at the factory and continues for the life of system 1. The second count is a session counter, which can be reset by the operator and at any appropriate time. The non-resettable life-cycle count and the resettable session count are displayed on display 170 as explained previously, and are selectable with mode button 176.

As noted earlier, display port 178 displays three colors, green—if all functions are working properly, red—if a motor-overload or low-battery voltage condition exists, or blinking—when the battery condition is low but still functioning. Display port 178 is connected to microprocessor 272. Plus or up button 172, minus or down button 174 and mode or mode/jog button 176 are shown as being attached to microprocessor 272. These are all mounted on a keypad 288.

The direction of motor 74 is controlled by four switches in an "H" configuration, these four switches being numbered 290, 292, 294 and 296. Motor 74 runs in the forward direction when switches 290 and 294 are in the "ON" condition and switches 292 and 296 are in the "OFF" condition. Motor 74 reverses its direction when the current changes direction by turning switches 292 and 296 ON, and switches 290 and 294 OFF. All of these signals are generated and delivered from microprocessor 272.

As explained previously, the electrical power for injection system 1 is provided by battery 11. Battery 11 is advantageously rechargeable, and a recharging device can be in addition to hypodermic injection system 1.

The present invention has many attributes not heretofore known in hypodermic injection systems for injecting large numbers of animals or humans. Some of the many features are set forth below, and other features are also described below.

The system has removable injection heads, allowing for a wide range of deliverable volumes of injectate. Each head has a range of injectate volumes available therefrom, and the user can select a volume available from each head, and the control in the direct drive system will deliver the selected volume;

alternatively, a repeatable, fixed volume is also available—and the volumes can be obtained at a rapid rate.

A remote handpiece for use with a fluid supply at the main housing is provided. The fluid is supplied either through a connecting tube or the fluid supply and valve system can be located at the remote handpiece. The connecting tube can be a hydraulic system with two piston assemblies for transferring power from the main housing to the remote handpiece, or alternatively by using a two-part cable with a push/pull or rotational action.

The clamping assembly moves from a closed position (for protecting against dirt and various damaging and unsanitary materials) to an open position for receiving a body part, and then to a closed position to make the injection. The clamp assembly facilitates the injection into the backside of an ear cartilage.

The embodiments described above use a special hub on the perforator assembly. This assures that the system cannot be used with standard needles for avoiding the serious problems which can occur if standard needles are used for making injections in animals or humans. The system cannot work even if one were to attempt to use a standard needle hub, whose contours are set by the International Standards Organization ("ISO").

The injector system can provide means for only allowing a particular compound or series of compounds in the septum. For some injectates, such as for example immuno-sterile injectates, it is extremely important that the injectate not be used at the wrong time. Therefore, an electronic system can be employed which matches the injection head with a bottle of the particular injectate. If the required injection-head bottle is not properly matched, a warning signal is made on the display and the system is disabled from making an injection. Both the head and the bottle are electronically coded, and they send coding signals to the microprocessor. The microprocessor either enables the injection or effects a warning signal and disables the injection apparatus.

The use of a flexible hub interface or a swivel discourages the bending of the perforator if an animal to which an injection is being given moves sideways. This prevents damage to sidewise bending torque to the perforator shaft during an injection shot.

As suggested in this disclosure, the injection system can be programmed to make a particular injection with communication through radio frequency signals emitted from a transmitter/receiver on an animal. One such example is shown in FIG. 1 where a typical dairy cow 2 has an ear tag sensor 4 which will communicate with injector 1 to provide useful information such as body temperature to help identify the fertility cycle. Other information is also possible with the ear tag or other sensors appropriately located on or in the body, another example being a location in the digestive system of the animal.

The description above described the two-trigger system that will discontinue the forward movement of the injection ram if either trigger is released, but will thereafter continue the injection process when the disengaged trigger (or triggers) is re-engaged. It is noted that such system can be adapted to disable the finger trigger, while maintaining the nose trigger only. This procedure allows for the use of a fixture for a stationary injection system to which an animal can be brought to the nose trigger to receive an injection. The fixture could be made to hold the main injector housing or a remote handpiece, but in either case, the finger trigger is no longer active.

The nose shield was provided for enabling an injection only if an animal or human is stationary enough to properly receive an injection. The nose shield can be released after the finger trigger is actuated or only with actuation of the nose shield while the finger trigger is actuated. Alternatively, since the injector system is electrically operated, release of the nose shield can be accomplished by the pulling away of a solenoid shaft or a reverse magnetic field can be used to reverse a magnetic hold on the shield.

As mentioned earlier, one wants to prevent leak-back from the injection site in a body that has been injected. Means are described for further enhancing this outcome by having the injection hole momentarily sealed using a surface contact foam pad or shutter assembly at the injection site.

It was stated above that a cartridge holding an injectate could be used with the inventive injection system. As explained therein, this includes a lyophilized cartridge. Lyophilized cartridges can be inserted in place of the otherwise permanent injection chamber, where the mixing of the injectate components occurs at the pull-back of the drive ram, the injection being made either as a single shot or progressively in the forward direction in a stepwise or jog fashion. The small, light weight and very mobile delivery head at the end of the extended tube, along with the small dose step-wise delivery for each jog movement forward, is especially useful when working with piglets or other small animals where the dose is often quite small; wherein, the need for a complete refill between animals is advantageously eliminated. These features have exceptional utility in human applications for mesotherapy or plastic surgery procedures.

Other features involve the structure for stopping an injection if the target moves away. The injection system is capable of very high rates of injection, and protection has been provided to avoid overheating of the motor. The temperature of the body of an animal or human can be monitored, and amongst the uses of this information is whether or not to make particular injections. A microprocessor is employed for controlling the injection system, providing fast, reliable control over a wide area based on a variety of factors. A magazine is provided for the storage and safe, easy insertion of perforator assemblies, and for the safe storage of used assemblies. A new bottle mounting technique is part of the inventive concept. Provision is made for low-battery charge protection. Very high numbers of injection shots, in the thousands of shots, can be made without any need for an external power supply. An orientation assembly is included in one of the embodiments described above for preventing air from being pulled into the injection chamber. Cycle counters are provided for counting injections made under a variety of conditions. The injection system according to the invention facilitates the reduction of pain to animals and to humans. The display used is easy to read and easy and effective in operation.

Although the invention has been shown and described in embodiments having needles or perforators, it is within the purview of the invention that its teachings can be utilized and embodied in needle-less devices.

The invention has been described in detail with particular emphasis on the embodiment discussed above, but variations and modifications may occur to those skilled in the art from the preceding description and the claims to follow.

We claim:
1. A hypodermic injection system for removing injectate from an injectate supply for injection into subcutaneous, intramuscular or intradermal region of a body, said injection system comprising:
   a removable and replaceable injection head operatively attachable to an injectate supply, said injection head including:

an injectate chamber for receiving injectate to be injected into a body;

an assembly-holding device for holding an orifice exit nozzle to receive injectate from said injectate chamber and for delivering injectate to the body; and a drive system including:

a ram device for applying pressure to injectate in said injectate chamber while moving in a forward direction from an initial position to force a first settable amount of injectate into the exit nozzle and into the body, and for relieving the pressure upon completion of an injection and establishing a low pressure in said injectate chamber to effect the transfer of a second settable amount of injectate from the injectate supply to said injectate chamber;

a volume restrictor settable according to a volume signal for limiting the distance said ram device is moved out of said injectate chamber to achieve a desired dosage of injectate; and a main actuator assembly operatively connected to a motor for actuating said motor.

2. A hypodermic injection system according to claim 1 wherein said injection head includes structure for operatively connecting said injection head to a direct-drive housing, said injection head being detachable from said direct-drive housing and being replaceable with at least one different injection head having an injectate chamber of a different size to adapt said injection system to hold different amounts of injectate.

3. A hypodermic injection system according to claim 1 wherein said removable and replaceable injection head further comprises its own nose actuator operatively communicating with said motor, said motor being actuated in response to the simultaneous actuation of said main actuator by a user and said nose actuator by contact with the body to be injected.

4. A hypodermic injection system according to claim 1 wherein the injectate supply is a vial for holding injectate, the vial having an open end covered with a pierceable septum, and wherein said injection system further comprises a removable vial carriage adapted to a particular size vial for operatively holding the vial, said vial carriage comprising:

a vial carriage mount assembly on said injection system for supporting the vial with the end of the vial covered with the septum being located on a predetermined path;

a hollow septum spike fixed on said removable vial mount carriage located on said injection system and having a free sharp end located on the predetermined path and a base, the vial being movable along the predetermined path with the vial end facing said septum spike for enabling said septum spike to pierce the septum; and structure for securing the vial in a secure position while retaining a secure fluid seal with the vial end, with the septum across the vial end having been pierced with said septum spike.

5. A hypodermic injection system according to claim 1 wherein said hypodermic injection device includes a remote injection and control device, said remote injection and control device comprising:

a remote injection assembly, said remote injection assembly including:

a remote exit nozzle assembly-holding device for placing the exit nozzle in contact with the body and for discharging injectate into the body; and a remote actuation device remote from said filling device for actuating said motor and said drive system to discharge injectate from the holding device; and an extension apparatus for operatively connecting said remote injection assembly to said injection head.

6. A hypodermic injection system according to claim 1 and further including:

a direct-drive housing for housing said ram device, said direct-drive assembly including attaching structure for selectively attaching one of said injection heads having different sizes of injection chambers to said direct-drive housing;

a mode sensor for sensing the size of the injection head attached to said direct-drive housing, and a control system for controlling the operation of said injection system, said control system comprising a control panel, said control panel including:

a display structure;

mode-indicating apparatus operatively interconnecting said mode sensor and said display structure; and a mode actuator for operating said mode-indicating apparatus to effect the display of the size of the injection chamber in the injection head attached to said direct-drive housing.

7. A hypodermic injection system according to claim 1 and further including:

volume control apparatus for varying the volume of each dosage of injectate discharged by said injection system, said volume control apparatus comprising:

a ram-operation with a rearward most pre-injection position settable for controlling the volume of injectate to be delivered prior to application of pressure to injectate in said injectate chamber; and a volume control electronic system for setting said ram-operation device the rearward most pre-injection position according to the volume of injectate desired for each dosage.

8. A hypodermic injection system according to claim 1 wherein the injectate supply is selected from one of a vial attached directly to the top of the injection system for holding injectate, and a remote reservoir of injectate with a feed tube to the injection system, and wherein said injection system further comprises:

an orientation switch assembly for disabling operation of said filling device when the vial orientation located on top of the injection system would allow air to be drawn into the injectate flowing to said injectate chamber, and conversely for enabling operation of said filling device when the vertical orientation of said vial located on top of the injection system will not allow air to be drawn into said injectate chamber; and an orientation switch-disabling device for disabling said orientation switch when the injectate supply is the remote reservoir of injectate.

9. A hypodermic injection system according to claim 1 and further including:

an injection-counting sensor apparatus for measuring recording the number of injections given according to at least one criterion;

an electronic processor operatively connected to said injection-counting sensor apparatus; and an injection count display operatively connected to said electronic processor for displaying the number of injections measured by said injection-counting sensor apparatus.

10. A hypodermic injection system according to claim 9 wherein said injection-counting sensor apparatus comprises:

a life cycle injection-counting sensor for measuring the cumulative number of injections given by said injection system;

a session injection counting sensor for measuring the number of injections given within a predetermined session, said session injection-counting sensor being resettable at the end of the predetermined session; and wherein said injection count display displays both the counts measured by said life cycle injection-counting sensor and said session injection-counting sensor.

11. A hypodermic injection system according to claim 1 and further including injectate-refill apparatus for removing air from the injectate chamber when a new injectate supply is added to said injection system, said injectate-refill apparatus comprising:

a refill-actuation device operatively connected to said direct-drive assembly for actuating said direct-drive assembly in miniscule amounts to drive said ram device forward for miniscule distances to expel air from said system while said exit nozzle is held in an upward direction.

12. A hypodermic injection system according to claim 1 and further including:

a warning system for generating alert signals in response to certain defects in said injection system, said warning system comprising:

an injector sensor for sensing if the components of said injector head are functioning properly, and for generating an injector-alert signal if the components of said injector head are not functioning properly;

an electric energy source for providing electrical energy to said motor, and an electric-energy source sensor for sensing if said electric energy source is functioning properly, and for generating an energy source alert if said energy source is not functioning properly; and a warning display operatively connected to said injector sensor and to said electric-energy source sensor for displaying a warning signal in response to the generation of the injector-alert signal and/or the energy-source alert signal.

13. A hypodermic injection system according to claim 1 wherein exit nozzle is a perforator, each perforator having a hollow perforator exit path with a free end for discharging injectate, and wherein said injection system further includes a magazine assembly for holding said perforator, said magazine assembly comprising:

a perforator support for holding at least one new perforator device with the free end pointing in a particular direction;

a carriage for holding a new perforator device for presenting the new perforator device for attachment to said perforator assembly-holding device holding structure of said injection head;

a chamber for holding used perforator devices in a non-contaminating manner;

an access port to said chamber for inserting used perforator devices into said chamber; and a new perforator-moving device for moving in sequence new perforator devices from said support to said carriage;

wherein said carriage presents a new perforator device to said perforator-device holding structure and cooperates with said holding structure to removably fix said new perforator device to said holding structure, and wherein used perforator devices are inserted into said access port.

14. A hypodermic injection system according to claim 1 and further including a clamp assembly initially in a closed position for eventual clamping a loose body part to receive an injection, said clamp assembly comprising:

a first clamping device;

a second clamping device opposite said first clamping device and being movable from the closed position to an open position with respect to said first clamping device for inserting the loose body part between said first and second clamping devices in preparation for receiving an injection from said injection system; and a moving apparatus for then moving said second clamping device with respect to said first clamping device to the closed position to therein provoke an injection.

15. A hypodermic injection system according to claim 14 wherein said injection system further includes a nose actuator operatively connected to said motor for sending an actuation signal to effect the operation of said motor in response to the actuation of said nose actuator by contact with the body to be injected, and a nose shield for protecting said exit nozzle on said nose actuator, said nose shield having an attached end for attachment to said injection head and a free end, and wherein said first clamping device comprises the free end of said nose shield and said moving apparatus comprises a handle for moving said second clamping device.

16. A hypodermic injection system according to claim 15 wherein said second clamping device comprises a soft, pliable pad against for the body part to engage during an injection, said pad yielding to expansion of the body part as injectate enters the body part.

17. A hypodermic injection system for removing injectate from an injectate supply for injection into a body, said injection system comprising:

a housing;

a detachable head for operative attachment to said housing, said detachable head comprising:

an injection chamber for receiving injectate from the injectate supply; and an exit nozzle for receiving injectate from said injection chamber for injection into a body;

a device for transferring injectate in said injection chamber in response to a positive pressure on injectate in said injection chamber; and a motor drive assembly for establishing the positive pressure, said motor drive system including a reciprocal ram device for moving in one direction to apply the positive pressure to injectate in said injection chamber to force injectate into said exit nozzle for injection into a body, and for moving in the opposite direction to relieve said positive pressure upon completion of an injection in preparation for the next supply of injectate in said injection chamber.

18. A hypodermic injection system according to claim 17 wherein said variable volume injection chamber for receiving injectate is adapted to receive an independent and replaceable cartridge holding injectate, the injectate to be discharged from the replaceable cartridge with the application of high pressure to said injection chamber.

19. A hypodermic injection system according to claim 18 wherein the cartridge is adapted to hold a lyophilized medicine, said cartridge being inserted into said chamber, and wherein said system includes apparatus for mixing the material in the lyophilized cartridge in a selected one of upon insertion of the cartridge into said injection chamber and upon movement of said ram device from the one direction to the opposite direction.

20. A hypodermic injection system according to claim 19 wherein said lyophilized cartridge for insertion into said chamber includes apparatus for moving said ram device in the one direction for selectively forcing injectate from the cartridge as a single dose shot and or alternatively progressively in shots smaller than the single dose shot.

21. A hypodermic injection system according to claim 17 and further including electronic sensors for determining variable factors of a body and for generating sensor signals in response to the factors, and a microprocessor operatively communicatively connected to said electronic sensors for generating output signals in response to said respective sensor signals.

22. A hypodermic injection system according to claim 21 wherein at least one of said sensors detects at least one parameter indicative of the fertility cycle of the body, and a display operatively connected to said microprocessor for displaying an indication of the fertility cycle of the body.

23. A hypodermic injection system according to claim 21 wherein said electronic sensors are selected from the group consisting of radio frequency sensors.

24. A hypodermic injection system according to claim 17 and further including an injectate supply sensor for generating an electronic signal responsive to the acceptability or non-acceptability of an injectate supply for said system, and a microprocessor operatively connected to supply sensor for disabling said system in response to a non-acceptable injectate supply.

25. A hypodermic injection system according to claim 17 wherein said exit nozzle comprises a replaceable perforator assembly having a hollow perforator shaft with an orifice to discharge injectate.

26. A hypodermic injector system according to claim 25 wherein said perforator assembly comprises a hub for holding said perforator shaft, said hub differing from hubs for holding standard length needles to prevent use of standard length needles in said system.

27. A hypodermic injection system according to claim 17 and further including a remote injection system operatively connectable to said injection head, said remote injection system being actuatable for injecting a body at a position remote from said detachable head.

* * * * *